(12) United States Patent
Samsoondar

(10) Patent No.: US 9,999,884 B2
(45) Date of Patent: *Jun. 19, 2018

(54) DISPOSABLE CARTRIDGE

(71) Applicant: INVIDX CORP., Markham (CA)

(72) Inventor: James Samsoondar, Markham (CA)

(73) Assignee: INVIDX CORP. (CA)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/680,736

(22) Filed: Aug. 18, 2017

(65) Prior Publication Data
US 2018/0126373 A1 May 10, 2018

Related U.S. Application Data

(63) Continuation of application No. PCT/CA2017/050584, filed on May 16, 2017, and a
(Continued)

(51) Int. Cl.
*B01L 3/00* (2006.01)
*G01N 33/86* (2006.01)

(52) U.S. Cl.
CPC ............. *B01L 3/502* (2013.01); *G01N 33/86* (2013.01); *B01L 2200/025* (2013.01); *B01L 2200/0605* (2013.01); *B01L 2200/0684* (2013.01); *B01L 2300/042* (2013.01); *B01L 2300/043* (2013.01); *B01L 2300/046* (2013.01); *B01L 2300/0816* (2013.01); *B01L 2300/0867* (2013.01);
(Continued)

(58) Field of Classification Search
CPC ............. Y10T 436/2575; Y10T 436/11; Y10T 436/25; B01L 2200/10; B01L 2300/045; B01L 2300/0816; B01L 2300/0867; B01L 2300/087; B01L 3/502; B01L 2200/0605; B01L 2400/0487; B01L 2400/0688; B01L 2300/042; B01L 2300/046; B01L 2200/0684; B01L 2200/025; B01L 2300/043; G01N 33/86
See application file for complete search history.

(56) References Cited

U.S. PATENT DOCUMENTS 4,514,091 A 4/1985 Kaspar et al.
4,722,714 A 2/1988 Marbourg, Jr.
(Continued)

FOREIGN PATENT DOCUMENTS

CA 2911318 A1 11/2015
WO 2016/049545 A1 3/2016

OTHER PUBLICATIONS

International Search Report and Written Opinion in International Application No. PCT/CA2017/050584, dated Jan. 15, 2018.

*Primary Examiner* — Sally A Merkling
(74) *Attorney, Agent, or Firm* — J.A. Lindeman & Co., PLLC

(57) ABSTRACT

A disposable cartridge for rapidly metering a sample for measuring a property of the sample is described. The cartridge can receive a sample when it is in an unsealed configuration, and a cap is used to facilitate metering of the sample and sealing the cartridge. When the cartridge is in a sealed configuration, pressurized air is used to push the metered sample into a chamber containing at least one reagent, and subsequently into a detection chamber for measuring a property of the sample.

20 Claims, 16 Drawing Sheets

Related U.S. Application Data continuation-in-part of application No. 15/356,630, filed on Nov. 20, 2016, now Pat. No. 9,821,307.

(60) Provisional application No. 62/258,520, filed on Nov. 22, 2015.

(52) U.S. Cl.
CPC ............ *B01L 2400/0487* (2013.01); *B01L 2400/0688* (2013.01)

(56) References Cited

U.S. PATENT DOCUMENTS

| | | |
|---|---|---|
| 6,750,053 B1 | 6/2004 | Opalsky et al. |
| 7,682,833 B2 * | 3/2010 | Miller ............... B01L 3/502707 422/537 |
| 9,470,673 B2 | 10/2016 | Samsoondar |
| 2010/0196908 A1 * | 8/2010 | Opalsky ................ B01L 7/52 435/6.1 |

* cited by examiner

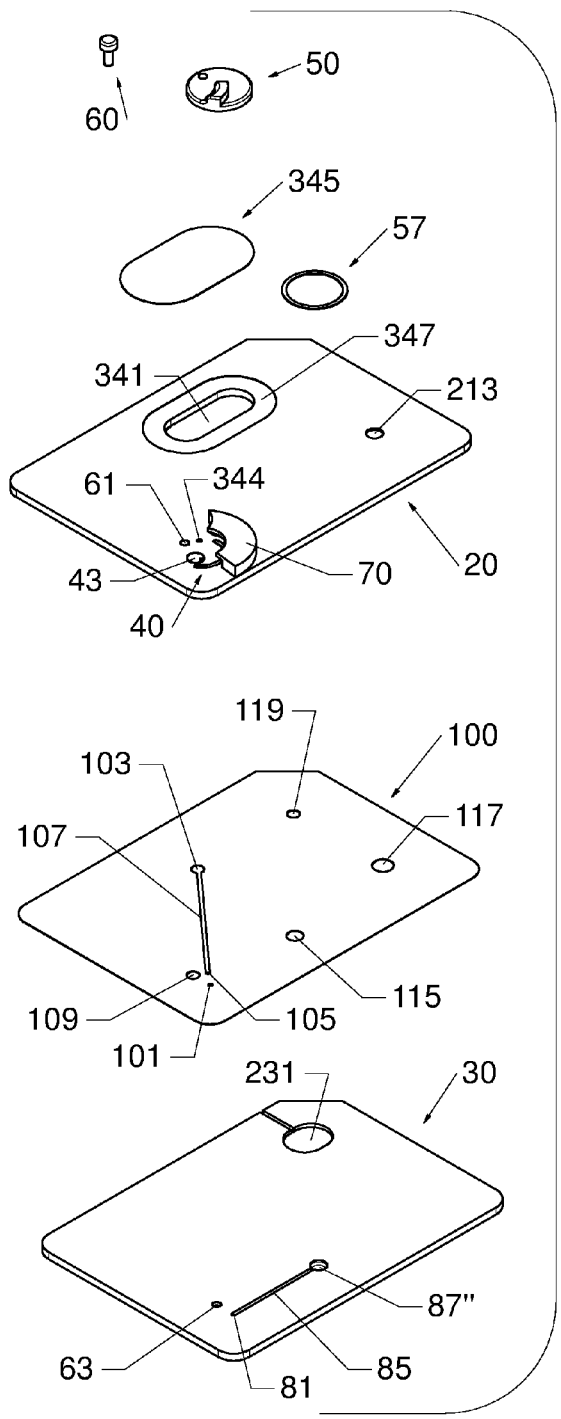
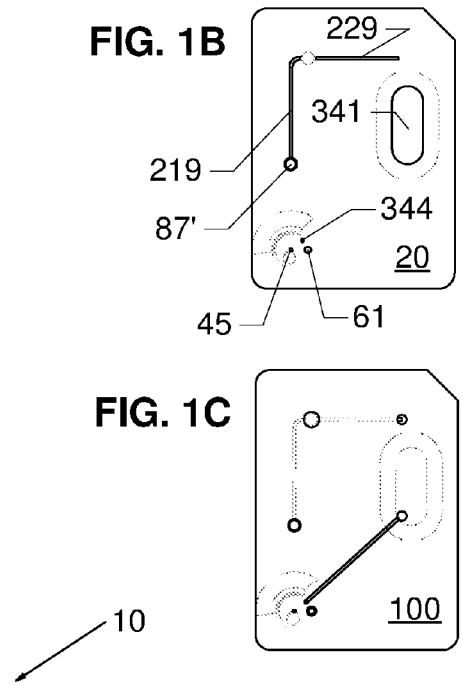
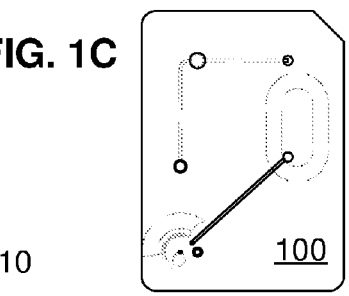
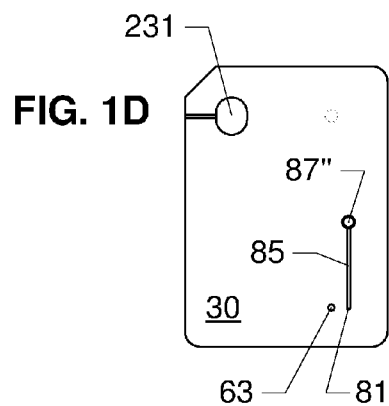
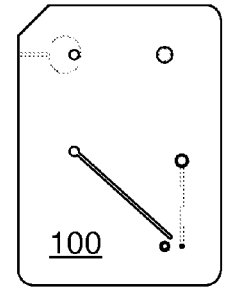

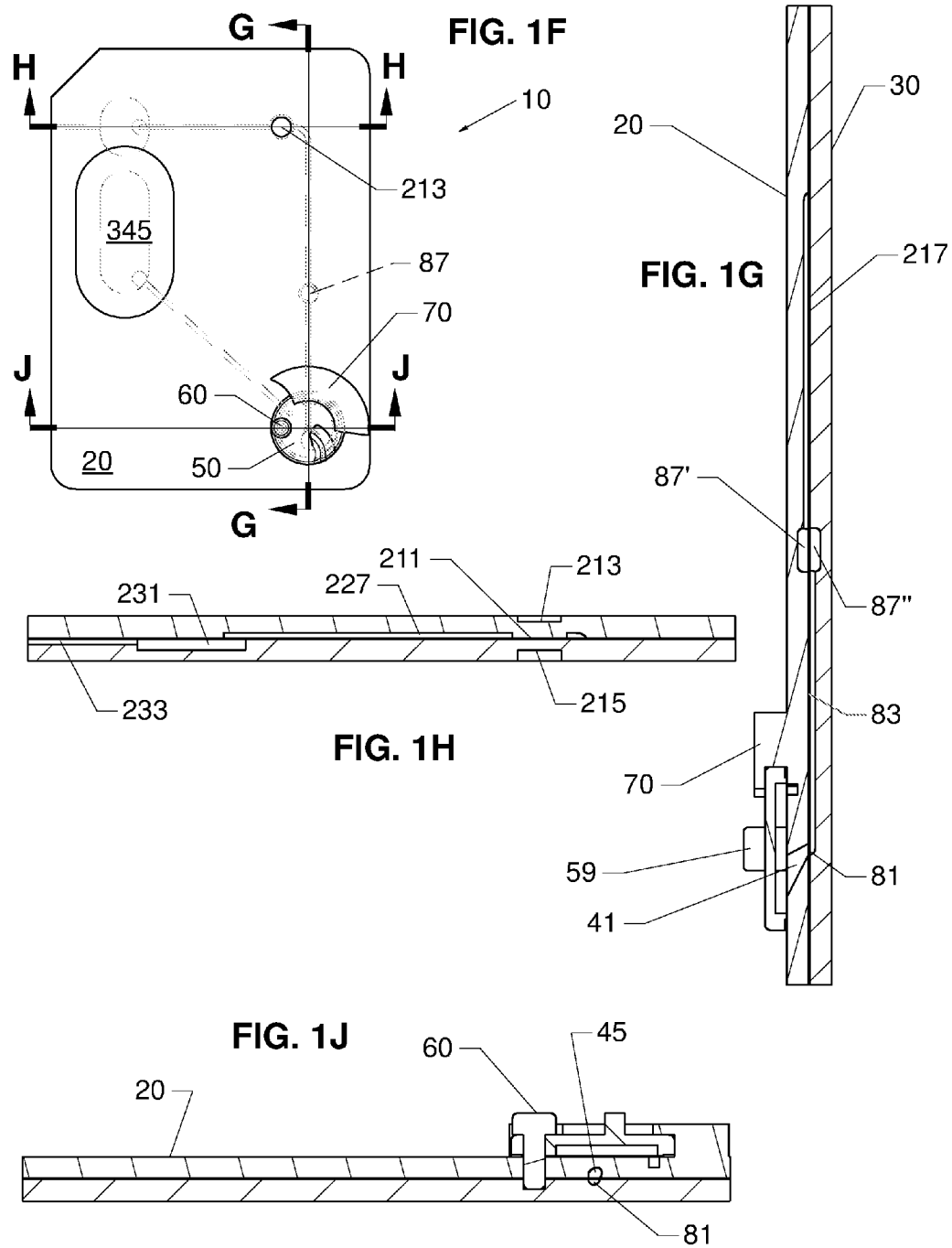

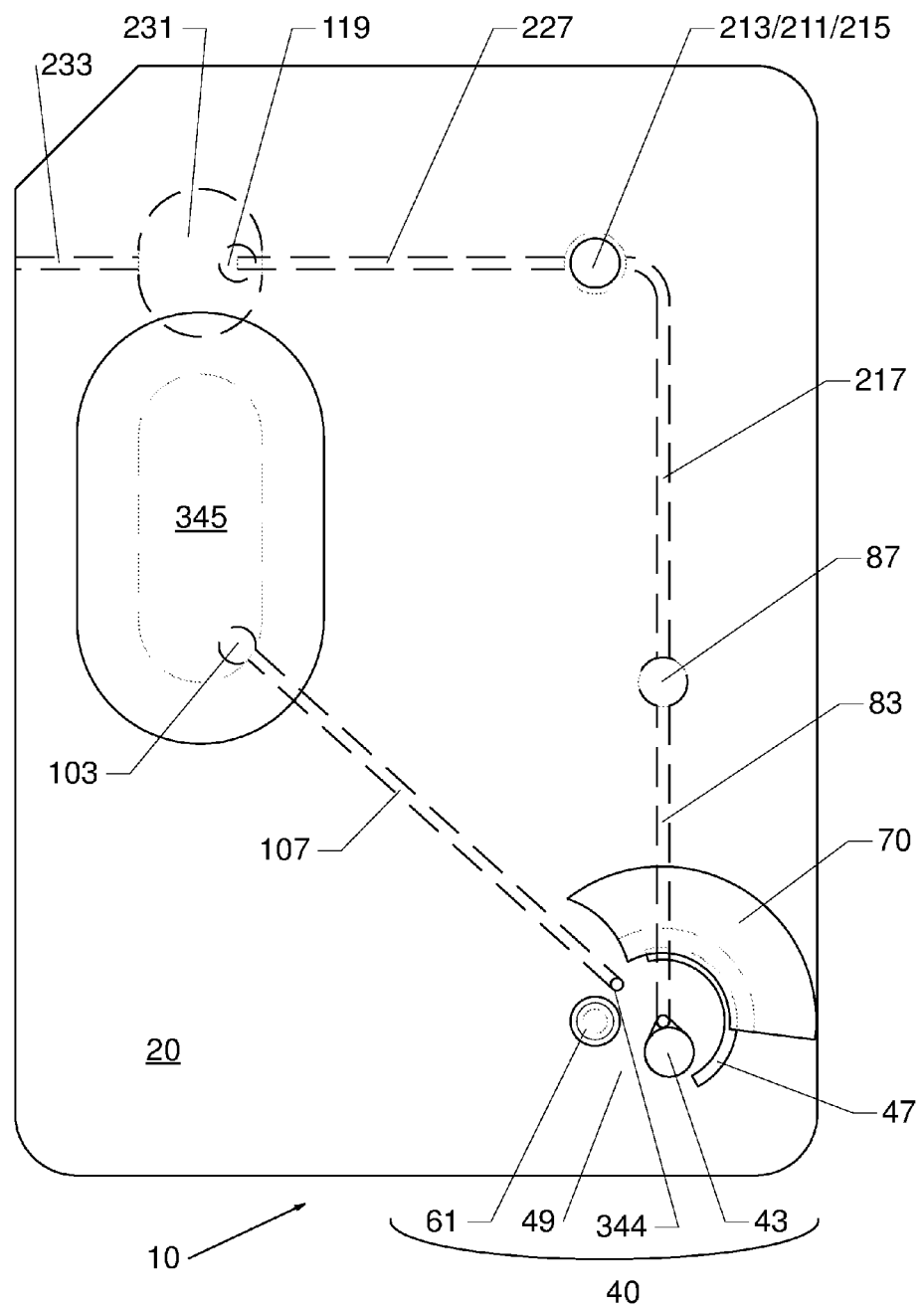

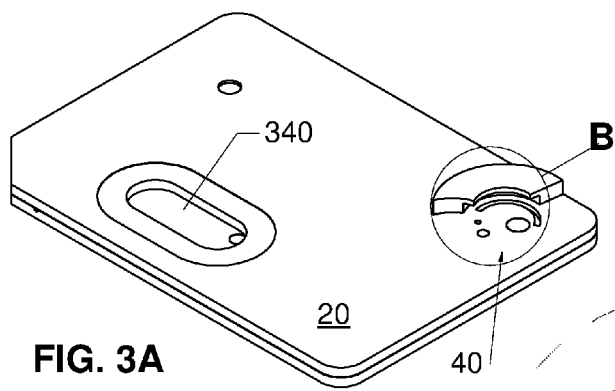
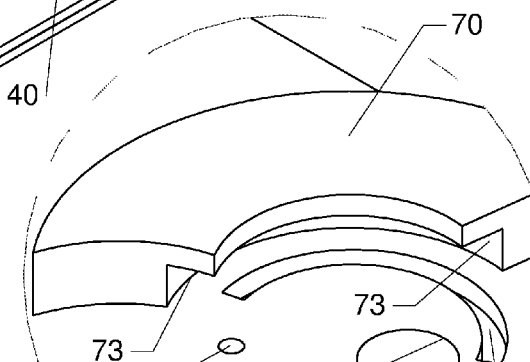
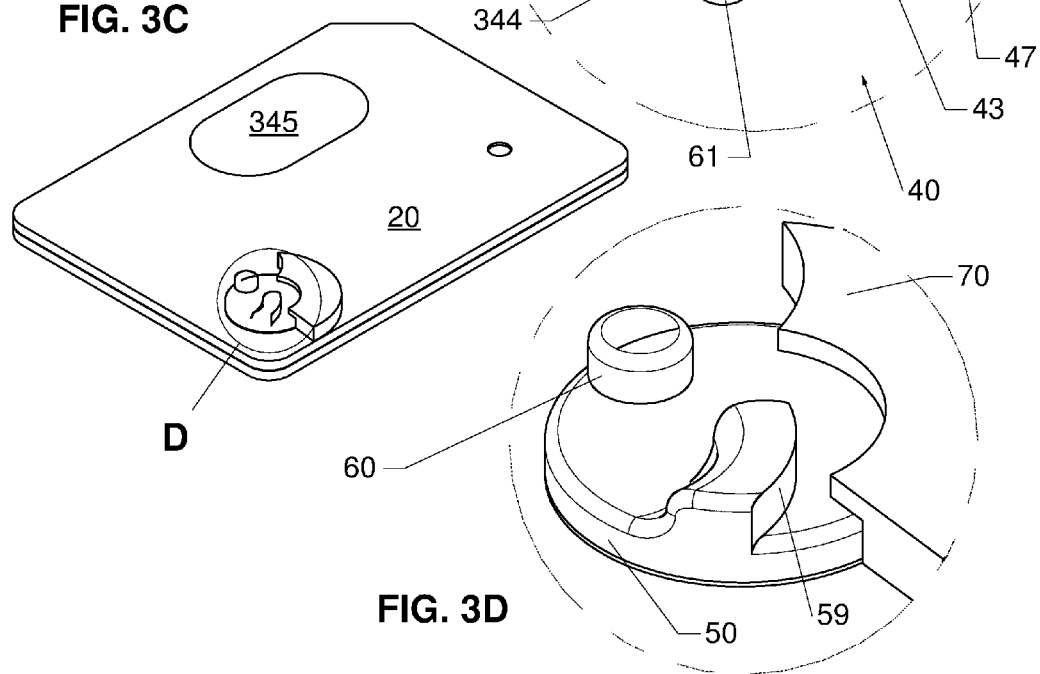

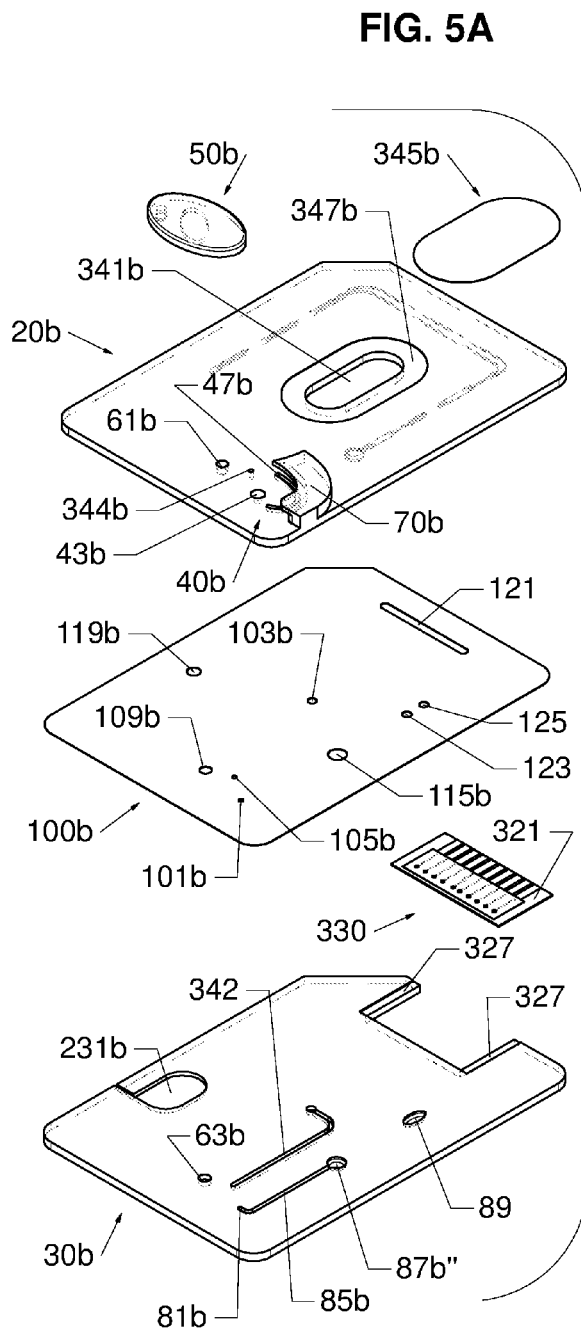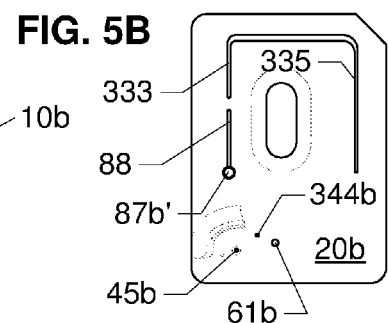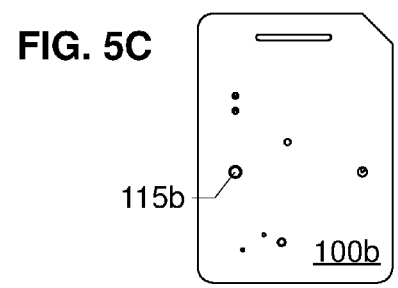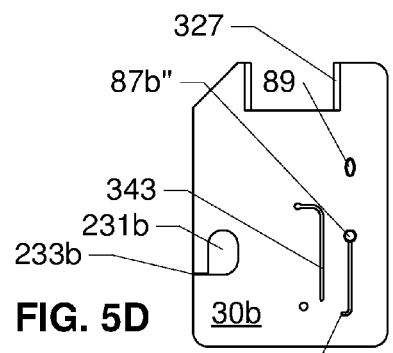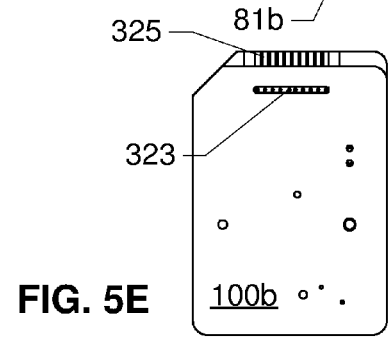

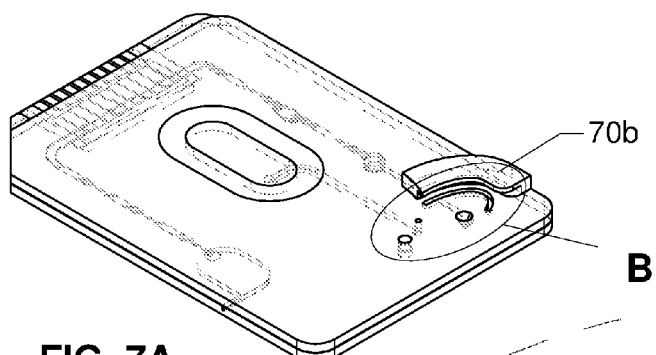
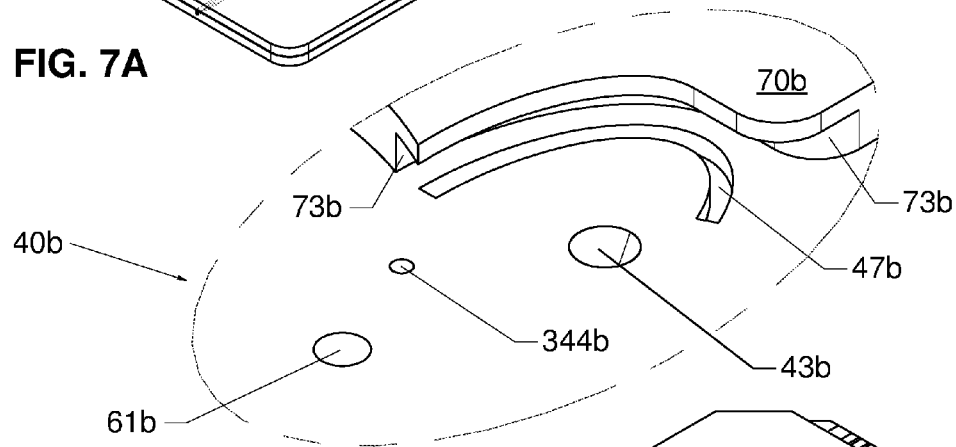
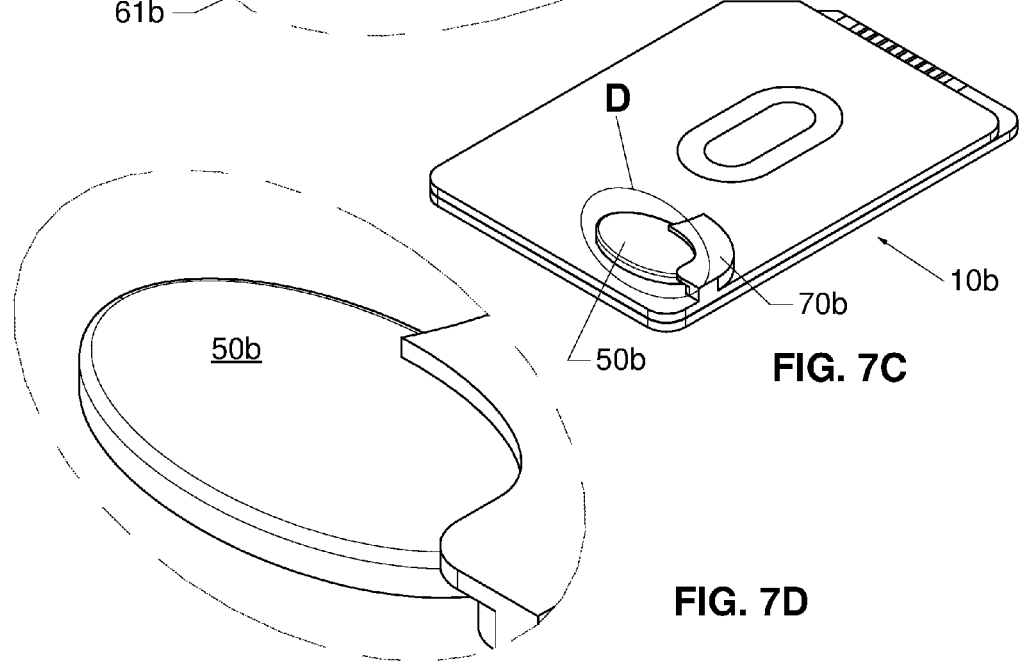

FIG. 8A
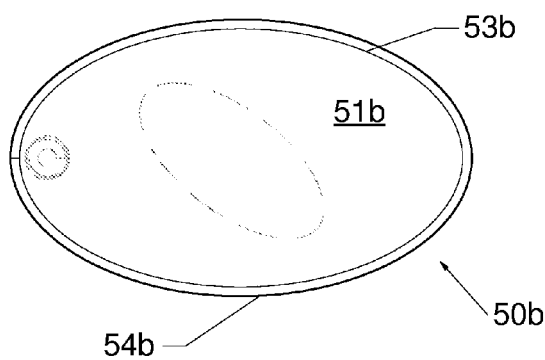
FIG. 8B
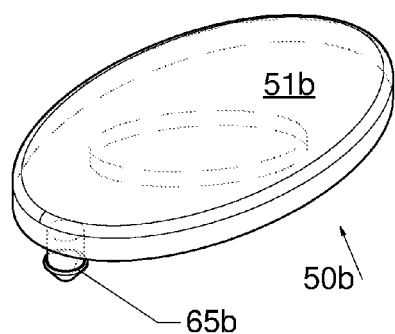
FIG. 8C
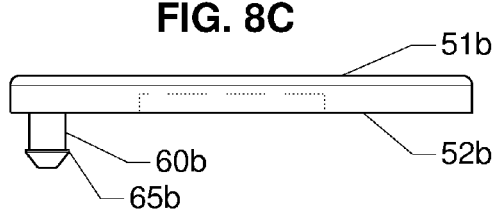
FIG. 8D
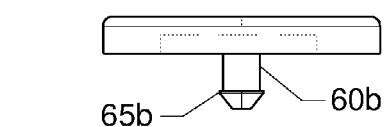
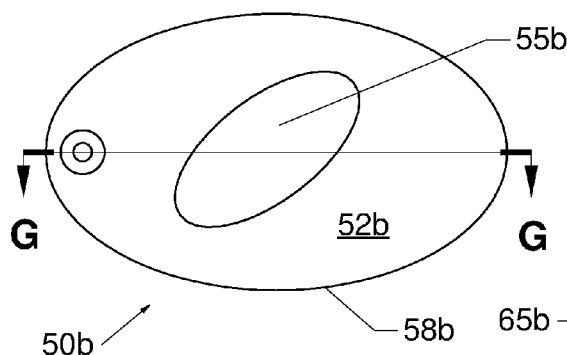
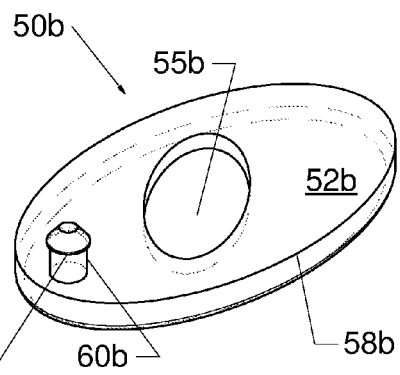
FIG. 8E
FIG. 8F
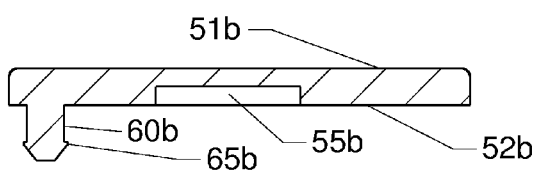
FIG. 8G

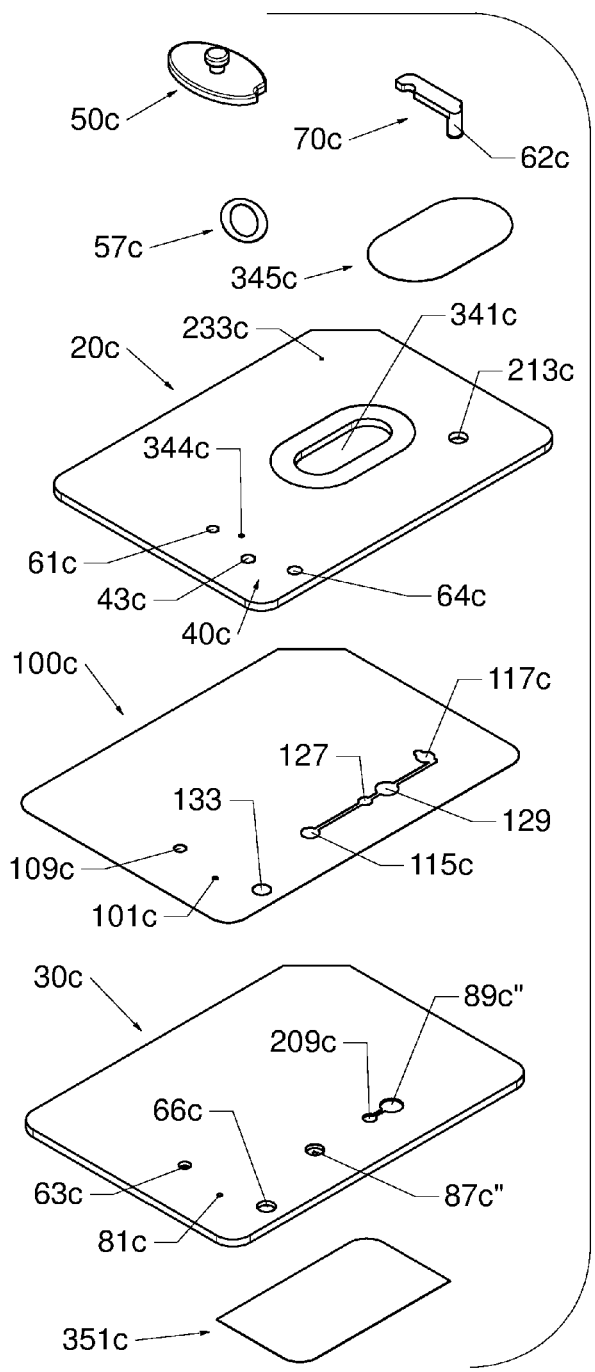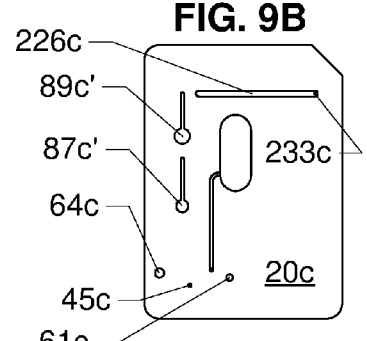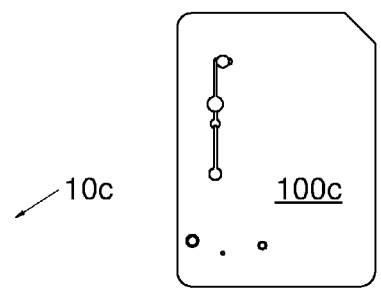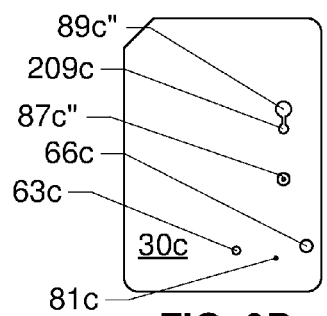

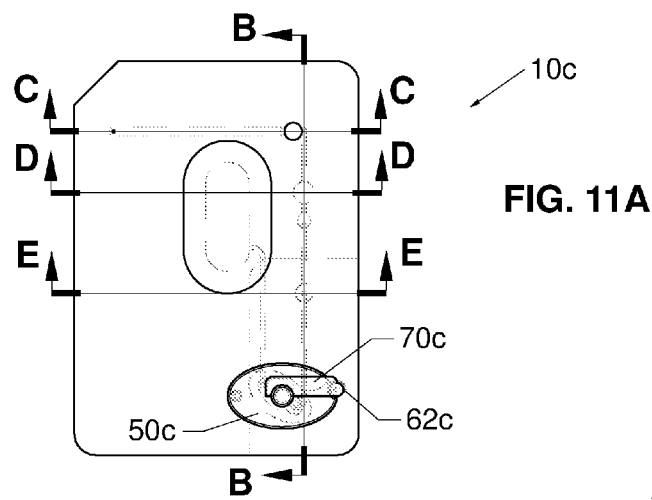
FIG. 11A
FIG. 11B
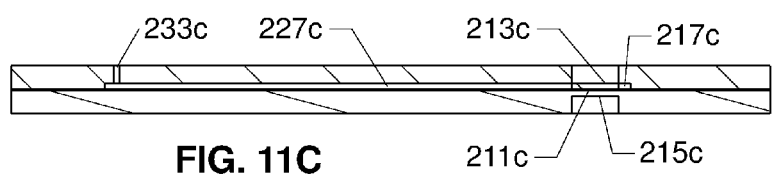
FIG. 11C
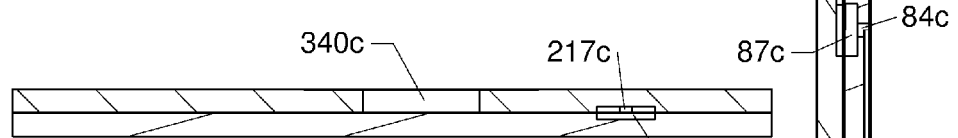
FIG. 11D
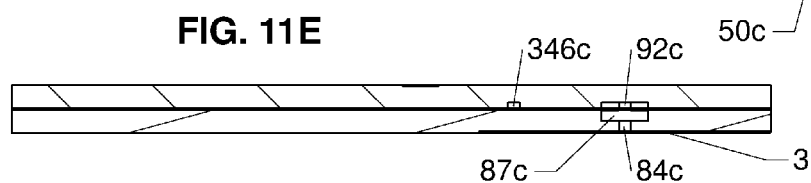
FIG. 11E

DISPOSABLE CARTRIDGE

FIELD OF THE INVENTION

The invention relates to a disposable cartridge used for measuring a property of a sample. The disposable cartridge is useful for point-of-care testing (POCT).

BACKGROUND OF THE INVENTION

The result of reaction between a liquid sample and one or more reagent, preferably dry, depends on the quantity of the one or more reagent and the volume of liquid sample. Although any type of liquid sample is implied, serum, plasma and blood (also referred to as whole blood) are samples of particular interest. When blood is allowed to clot and the sample is centrifuged, the yellow liquid that sits on top of the blood clot is called serum. If the blood is collected in a tube containing an anticoagulant, for example heparin, and the sample is centrifuged, the yellow liquid that sits on top of the packed red blood cells is called plasma. The packed red cell volume (PCV) or hematocrit determines the percentage of red blood cells (RBCs) in whole blood. Since only the RBCs contain hemoglobin, total hemoglobin is highly correlated with hematocrit, except in cases of for example, macrocytic anemia where the mean red cell hemoglobin concentration is lower than that of a normal red cell. Some analyzers measure hematocrit by electrical conductivity, and convert the hematocrit measurement to a total hemoglobin concentration, and some analyzers measure total hemoglobin concentration by spectroscopy, and convert the total hemoglobin concentration to a hematocrit value. Spectroscopic calibration algorithms can be developed to measure both hematocrit and total hemoglobin concentration.

Point-of-care Testing (POCT) is defined as medical diagnostic testing performed outside the clinical laboratory in close proximity to where the patient is receiving care. POCT is typically performed by non-laboratory personnel and the results are used for clinical decision making. For the sake of convenience and rapid turnaround time, blood is the sample of choice. Due to the complexity of blood, certain tests can only be performed on serum or plasma.

POCT has a range of complexity and procedures that vary from manual procedures to automated procedures conducted by portable analyzers. POCT is most efficient when the sample of interest can be applied to or loaded onto a test cartridge, the sample inlet capped, and the remaining steps are performed automatically after the loaded test cartridge is inserted into a slot or receptor of an analyzer. Some blood tests, for example coagulation assays and immunoassays require a fixed volume of sample, for example, to ensure that when mixed with a reagent the ratio of the volume of sample to the volume of the reagent is held constant. Other tests, for example that determine electrolytes, do not require a fixed volume of sample. In the case of electrolytes, sample volume may not be an issue if the electrolyte concentration is estimated by measuring electrical activity in the sample.

Applying an unmetered sample volume to test strips is well known; some test strips contain absorbing sections that can accommodate a known volume of plasma, after the red cells are retained in another section of the test strip near the blood application site. In some cases, the hematocrit affects the plasma flow in test strips, and therefore correction for hematocrit may improve accuracy of the analyte measurement. In some systems, a pipette is used that is designed to aspirate a predetermined sample volume.

U.S. Pat. No. 6,750,053 to Opalsky et al and U.S. Pat. No. 7,682,833 to Miller et al disclose devices for rapidly metering samples. U.S. Pat. No. 6,750,053 describes a snap-shut seal and states (column 11 lines 16-19) that the "volume of the metered fluid sample is the volume of the holding chamber 20 between the orifice (48 in FIG. 5) in the wall of the holding chamber and the capillary stop 22." U.S. Pat. No. 7,682,833 discloses (column 23 lines 39-43) that the "location at which air enters the sample chamber (gasket hole 27) from the bladder, and the capillary stop 25, together define a predetermined volume of the sample chamber. An amount of the sample corresponding to this volume is displaced into the first conduit when paddle 6 is depressed." In the cases of U.S. Pat. No. 6,750,053 and U.S. Pat. No. 7,682,833, while the fluid sample is metered, the sample in the sample collection well (illustrated in U.S. Pat. No. 6,750,053 as element 12 in FIG. 3) is wasted.

Sample size is a major consideration for POCT systems, especially when it is desirable to use a small drop of blood obtained by puncturing the skin of a body part; the sample is referred to as a pin-prick sample. With some patients, it is difficult to obtain a small drop of blood, therefore there is a need to avoid any blood wastage. This is particularly true for neonatal blood testing.

Prothrombin Time (PT) is an example of a coagulation test, which requires a fixed sample volume. PT is usually reported as PT-INR (PT-International Normalized Ratio). The result for a prothrombin time performed on a normal individual will vary according to variations between different types and batches of thromboplastins used. The INR was devised to standardize the results using an ISI (International Sensitivity Index) value. Each manufacturer assigns an ISI value for any thromboplastin they manufacture, Another factor which affects PT-INR when using whole blood, as is the case of POCT, is the hematocrit. Only plasma contains coagulation factors, but a whole blood sample has a variable number of red cells mixed in, depending on the patient's hematocrit. These red cells take up space in the test cartridge. The coagulation factors that are being tested, are all in the liquid part of blood, i.e., the plasma. Because patients have different hematocrits, each patient sample adds a different amount of liquid plasma to the cartridge, but the amount of thromboplastin in the test cartridge is fixed. In a patient with low hematocrit, the excess plasma volume dilutes the reagent i.e., thromboplastin, and slows clot formation, resulting in a falsely increased PT-INR. PT-INR measured in the laboratory usually uses plasma, and plasma measurement of PT-INR is considered the gold standard. Therefore, whole blood PT-INR measurement will differ from the laboratory PT-INR measurement, which uses plasma. For POCT of PT-INR, correction can be made for an average hematocrit value, but errors in the PT-INR will increase as the hematocrit value moves away from the average hematocrit value. POCT of PT-INR usually use biosensors (also referred to as electrochemical detectors) that in many cases do not provide hematocrit measurement because the blood clots within seconds, after the blood is mixed with the thromboplastin.

SUMMARY OF THE INVENTION

The invention relates to a disposable cartridge for measuring a property of a sample. The disposable cartridge is useful for point-of-care testing (POCT). The disposable cartridge provides for automatic sample volume metering so that after applying an unknown sample volume to the cartridge, a specific volume of the sample is used for measuring the property of the sample.

As described herein there is provided a disposable cartridge comprising, a cartridge body comprising an upper surface and a lower surface;

a cap pivotally connected to the cartridge body by a pin, the cap positioned on the upper surface of the cartridge body, the cap comprising a top side and an underside, the underside comprising a cap recess surrounded by a flat surface;

a sample inlet portion located on the upper surface, the sample inlet portion comprising:

a sample storage well for storing a first portion of a sample, the sample storage well comprising a top portion for receiving the sample and a bottom portion for releasing a second portion of the sample to a sample storage conduit;

an air bladder exit port;

a pin hole for receiving the pin, and a sliding surface surrounding the sample storage well and the air bladder exit port, the sliding surface for frictionally engaging the flat surface of the underside of the cap;

the cap comprising a sweeping edge for skimming off any excess of the sample from the sample storage well or sample inlet portion when the cap is pivotally rotated from an open position where the cartridge is in an unsealed configuration, to a closed positioned where the cartridge is in a sealed configuration;

an air bladder fluidly connected with the air bladder exit port;

the sample storage conduit in fluid communication between the bottom portion of the sample well and a capillary break, the sample storage conduit for receiving the second portion of the sample, the total volume of the sample in the cartridge in the sealed configuration is equivalent to the volume measured from the top portion of the sample storage well to the capillary break;

a detection chamber in fluid communication with the capillary break and the sample storage conduit via a detection chamber inlet conduit, the detection chamber for receiving a portion of the total volume of the sample from the sample storage conduit and for generating a signal during sample interrogation, the signal used to calculate a property of the sample; and a vent in fluid communication with the detection chamber, the vent for relieving pressure in the detection chamber;

wherein, in the unsealed configuration the sample storage well is open and available to receive the sample, and in the sealed configuration the cap recess facilitates provision of a closed air passage connecting the air bladder exit port and the sample storage well for communicating pressurized air from the air bladder to the sample storage well via the air bladder exit port, so that when the air bladder is pressed, the volume of the sample, or a portion thereof, is urged from the sample storage conduit into the detection chamber.

The sample inlet portion of the disposable cartridge as defined above may further comprise at least one cap stop, the cap stop for defining the unsealed configuration and the sealed configuration of the disposable cartridge. The top portion of the sample storage well of the disposable cartridge may be substantially larger than the bottom portion of the sample storage well. Additionally, the sample inlet portion may further comprises a sample overflow well for receiving excess sample.

The disposable cartridge as described above may further comprise a groove disposed at the underside of the cap in front of the sweeping edge of the cap, the groove for holding any excess sample.

The disposable cartridge as described above may also comprise a gasket positioned on the flat surface of the cap. The sweeping edge of the cap may be an outer edge of the gasket.

The disposable cartridge as described above may also comprise a latch for securing the cap when the cartridge is in the sealed configuration. The latch may be a stationary structure anchored in the sample inlet portion. Alternatively, the latch may be pivotally attached to the sample inlet portion.

Also described herein is the disposable cartridge, defined above, that further comprises a detection chamber inlet conduit containing at least one reagent and disposed between the sample storage conduit and the detection chamber, a mixing chamber disposed between an end of the sample storage conduit adjacent to the capillary break and the detection chamber, or both the detection chamber inlet conduit containing at least one reagent and disposed between the sample storage conduit and the detection chamber and the mixing chamber disposed between an end of the sample storage conduit adjacent to the capillary break and the detection chamber.

The disposable cartridge as described above may further comprise a reagent chamber containing at least one reagent, the reagent chamber disposed adjacent to the mixing chamber, whereby passage of the total volume of the sample through the reagent chamber produces a partially mixed sample comprising the at least one reagent, and passage of the partially mixed sample into the mixing chamber results in a more efficient mixing of the sample. The mixing chamber may be substantially larger than the reagent chamber. The at least one reagent of the disposable cartridge as described above may be selected from dry thromboplastin, celite or kaolin, and the sample is blood.

Also provided herein is a system for metering a sample and measuring a property of the sample, the system comprising a disposable cartridge and an analyzer, the disposable cartridge comprising a cartridge body comprising an upper surface and a lower surface, a cap pivotally connected to the cartridge body by a pin, the cap positioned on the upper surface of the cartridge body, the cap comprising a top side and an underside, the underside comprising a cap recess surrounded by a flat surface, a sample inlet portion located on the upper surface, the sample inlet portion comprising a sample storage well for storing a first portion of a sample, an air bladder exit port, a pin hole and a sliding surface surrounding the sample storage well and the air bladder exit port, the sample storage well comprising a top portion for receiving the sample and a bottom portion for releasing a second portion of the sample to a sample storage well conduit; the pin hole for receiving the pin, the sliding surface for frictionally engaging the flat surface of the underside of the cap; the cap comprising a sweeping edge for skimming off any excess of the sample from the sample storage well or sample inlet portion when the cap is pivotally rotated from an open position where the cartridge is in an unsealed configuration, to a closed positioned where the cartridge is in a sealed configuration; an air bladder fluidly connected with the air bladder exit port; the sample storage conduit in fluid communication between the bottom portion of the sample well and a capillary break, the sample storage conduit for receiving the second portion of the sample, the total volume of the sample in the cartridge in the sealed configuration is equivalent to a volume measured from the top portion of the sample storage well to the capillary break; a detection chamber in fluid communication with the capillary break and the sample storage conduit via a detection chamber inlet conduit, the detection chamber for receiving a portion of the total volume of the sample from the sample storage conduit and for generating a signal during sample interrogation, the signal used to calculate a property of the sample; a detection chamber inlet conduit disposed between the sample storage conduit and the detection chamber and containing at least one reagent, whereby passage of the total volume of the sample through the detection inlet conduit produces a partially mixed sample comprising the at least one reagent; and a vent in fluid communication with the detection chamber, the vent for relieving pressure in the detection chamber. Wherein, in the unsealed configuration the sample storage well is open and available to receive the sample, and in the sealed configuration the cap recess facilitates provision of a closed air passage connecting the air bladder exit port and the sample storage well for communicating pressurized air from the air bladder to the sample storage well via the air bladder exit port, so that when the air bladder is pressed, the volume of the sample, or a portion thereof, is urged from the sample storage conduit into the detection chamber;

the analyzer comprising a receptor for receiving the disposable cartridge; one or more than one processor for controlling the analyzer; means for activating the air bladder; and a detector for receiving the signal from the detection chamber and sending the signal to the one or more than one processor for transforming the signal into the property of the sample.

A method for measuring a property of a blood sample is provided. The method comprises, i) depositing a blood sample into the sample storage well of a disposable cartridge in an unsealed configuration; the disposable cartridge comprising a cartridge body comprising an upper surface and a lower surface, a cap pivotally connected to the cartridge body by a pin, the cap positioned on the upper surface of the cartridge body, the cap comprising a top side and an underside, the underside comprising a cap recess surrounded by a flat surface, a sample inlet portion located on the upper surface, the sample inlet portion comprising a sample storage well for storing a first portion of a sample, an air bladder exit port, a pin hole and a sliding surface surrounding the sample storage well and the air bladder exit port, the sample storage well comprising a top portion for receiving the sample and a bottom portion for releasing a second portion of the sample to a sample storage well conduit; the pin hole for receiving the pin, the sliding surface for frictionally engaging the flat surface of the underside of the cap; the cap comprising a sweeping edge for skimming off any excess of the sample from the sample storage well or sample inlet portion when the cap is pivotally rotated from an open position where the cartridge is in an unsealed configuration, to a closed positioned where the cartridge is in a sealed configuration; an air bladder fluidly connected with the air bladder exit port; the sample storage conduit in fluid communication between the bottom portion of the sample well and a capillary break, the sample storage conduit for receiving the second portion of the sample, the total volume of the sample in the cartridge in the sealed configuration is equivalent to the volume measured from the top portion of the sample storage well to the capillary break; a detection chamber in fluid communication with the capillary break and the sample storage conduit via a detection chamber inlet conduit, the detection chamber for receiving a portion of the total volume of the sample from the sample storage conduit and for generating a signal during sample interrogation, the signal used to calculate a property of the sample; a detection chamber inlet conduit disposed between the sample storage conduit and the detection chamber and containing at least one reagent, whereby passage of the total volume of the sample through the detection inlet conduit produces a partially mixed sample comprising the at least one reagent; and a vent in fluid communication with the detection chamber, the vent for relieving pressure in the detection chamber. Wherein, in the unsealed configuration the sample storage well is open and available to receive the sample, and in the sealed configuration the cap recess facilitates provision of a closed air passage connecting the air bladder exit port and the sample storage well for communicating pressurized air from the air bladder to the sample storage well via the air bladder exit port, so that when the air bladder is pressed, the portion of the total volume of the sample is urged from the sample storage conduit into the detection chamber;

ii) rotating the cartridge cap about the pin and skimming off excess blood and arranging the disposable cartridge in the sealed configuration to produce a sealed cartridge comprising the volume of the sample, iii) inserting the sealed cartridge into a receptor of an analyzer, the analyzer comprising, the receptor for receiving the disposable cartridge; one or more than one processor for controlling the analyzer; means for activating the air bladder; and a detector for receiving the signal from the detection chamber and sending the signal to the one or more than one processor for transforming the signal into the property of the sample;

iv) activating the air bladder to provide the pressurized air and move the total volume of the sample through one of the detection chamber inlet conduit and a reagent chamber, disposed between an end of the sample storage conduit adjacent to the capillary break and the detection chamber, containing the at least one reagent, thereby dissolving the at least one reagent into the blood to produce a mixture of the blood and the at least one reagent;

v) urging a portion of the mixture of blood and the at least one reagent into the detection chamber; and vi) measuring the property of the blood sample in the detection chamber using the analyzer.

Also provided herein is the method as described above wherein, the property of the blood sample being measured is prothrombin time, or activated clotting time, the detection chamber of the disposable cartridge comprises an optical chamber, and the analyzer comprises a source of electromagnetic radiation that is directed to the optical chamber; the detector is configured to collect electromagnetic radiation that is transmitted through the optical chamber, or reflected from the optical chamber; in the step of measuring, a pre-determined calibration algorithm is applied to the collected electromagnetic radiation to measure hematocrit of the blood sample to produce a hematocrit measurement; and the hematocrit measurement is used to correct the prothrombin time for an actual plasma volume in the blood sample. Furthermore, the at least one reagent may be dry thromboplastin, and the property of the blood that is measured is prothrombin time. Alternatively, the at least one reagent may be one of celite and kaolin, and the property of the blood that is measured is activated clotting time.

The disposable cartridge described herein reduces sample wastage. The disposable cartridge may be combined with optical measurement of PT-INR, and used to measure hematocrit on a POCT device after the blood sample has clotted in the optical chamber. This is achieved by using calibration algorithms that measure hematocrit and hemoglobin in a clotted blood sample residing within the optical chamber.

The description provides as examples of detection technology, optical measurement and electrochemical sensors, but these are examples only and other forms of generating signals and receiving generated signals for measuring an analyte are considered to be within the scope of the present invention.

Other aspects and features of the present invention will become apparent, to those having ordinary skill in the art, upon review of the following description of specific embodiments of the invention, which are provided as examples.

BRIEF DESCRIPTION OF THE DRAWINGS

A better understanding of the novel features and advantages of the present invention will be made by reading the detailed description of the preferred embodiments provided later, in conjunction with the accompanying drawings, in which:

FIG. 1A is an exploded top perspective view of disposable cartridge 10 for measuring a property of a sample, the cartridge having a rapid sample metering system, according to a first embodiment of the cartridge;

FIG. 1B is a bottom view of the first housing member 20 of the cartridge shown in FIG. 1A;

FIG. 1C is the bottom view of the first housing member 20 of the cartridge shown in FIG. 1B, overlaid by and in alignment with the gasket 100 shown in FIG. 1A;

FIG. 1D is a top view of the second housing member 30 of the cartridge shown in FIG. 1A;

FIG. 1E is the top view of the second housing member 30 shown in FIG. 1D, overlaid by and in alignment with the gasket 100 shown in FIG. 1A;

FIG. 1F is a top view of the cartridge 10 shown in FIG. 1A, with the cap 50 in a fully closed position;

FIG. 1G is a first enlarged cross-sectional view through the cartridge shown in FIG. 1F along line G-G;

FIG. 1H is a second enlarged cross-sectional view through the cartridge shown in FIG. 1F along line H-H;

FIG. 1J is a third enlarged cross-sectional view through the cartridge shown in FIG. 1F along line J-J;

FIG. 2A is a top view of the cartridge 10 shown collectively in FIGS. 1A-1J, with the cap 50 and pin 60 removed;

FIG. 3A is a perspective view of the cartridge 10 shown in FIG. 2A, with air bladder 340 open;

FIG. 3B is a detailed view of detail B of the cartridge shown in FIG. 3A, showing details of the sample inlet portion 40;

FIG. 3C is a perspective top view of the cartridge 10 shown in FIG. 2D;

FIG. 3D is a detailed view of detail D of the cartridge shown in FIG. 3C;

FIG. 5A is an exploded top perspective view of the disposable cartridge 10b for measuring a property of a sample, the cartridge having a rapid sample metering system, according to a second embodiment of the cartridge;

FIG. 5B is a bottom view of the first housing member 20b of the cartridge shown in FIG. 5A;

FIG. 5C is the bottom view of the first housing member 20b shown in FIG. 5B, overlaid by and in alignment with the gasket 100b shown in FIG. 5A;

FIG. 5D is a top view of the second housing member 30b of the cartridge shown in FIG. 5A;

FIG. 5E is the top view of the second housing member 30b shown in FIG. 5D, overlaid by and in alignment with the gasket 100b shown in FIG. 5A;

FIG. 7A is a perspective top view of the cartridge 10b (with the cap 50b removed shown in FIG. 6A;

FIG. 7B is a detailed view of detail B of the cartridge shown in FIG. 7A, showing details of the sample inlet portion 40b;

FIG. 7C is a perspective top view of the cartridge 10b shown in FIG. 6D;

FIG. 7D is a detailed view of detail D of the cartridge shown in FIG. 7C;

FIG. 8A is a top view of the cap 50b shown in FIG. 7C;

FIG. 8B is a perspective top view of the cap 50b shown in FIG. 8A;

FIG. 8C is a front view of the cap 50b shown in FIG. 8A;

FIG. 8D is a right side view of the cap 50b shown in FIG. 8A;

FIG. 8E is a bottom view of the cap 50b shown in FIG. 8A;

FIG. 8F is a perspective bottom view of the cap 50b shown in FIG. 8E;

FIG. 8G is a cross-sectional view through the cap 50b shown in FIG. 8E along line G-G;

FIG. 9A is an exploded top view of the disposable cartridge 10c for measuring a property of a sample, the cartridge having a rapid sample metering system, according to a third embodiment of the cartridge;

FIG. 9B is a bottom view of the first housing member 20c of the cartridge shown in FIG. 9A;

FIG. 9C is the bottom view of the first housing member 20c shown in FIG. 9B, overlaid by and in alignment with the gasket 100c shown in FIG. 9A;

FIG. 9D is a top view of the second housing member 30c of the cartridge shown in FIG. 9A;

FIG. 9E is the top view of the second housing member 30c shown in FIG. 9D, overlaid by and in alignment with the gasket 100c shown in FIG. 9A;

FIG. 11A is a top view of the cartridge 10c (similar to the view shown in FIG. 9F) with the cap 50c in a fully closed position, for illustrating the internal structure;

FIG. 11B is a first enlarged cross-sectional view through the cartridge 10c shown in FIG. 11A along line B-B;

FIG. 11C is a second enlarged cross-sectional view through the cartridge 10c shown in FIG. 11A along line C-C;

FIG. 11D is a third enlarged cross-sectional view through the cartridge 10c shown in FIG. 11A along line D-D;

FIG. 11E is a fourth enlarged cross-sectional view through the cartridge 10c shown in FIG. 11A along line E-E;

Figure 2B:
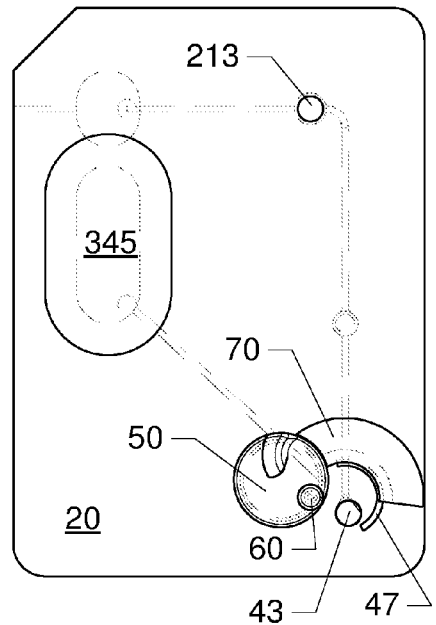
FIG. 2B is a top view of the cartridge 10 shown collectively in FIGS. 1A-1J, with the cap 50 in a fully open position.

For a better understanding of the present invention, and to show more clearly how it may be carried into effect, reference will now be made, by way of example, to the accompanying drawings, and which are described in the following detailed description of preferred aspects of the invention.

DETAILED DESCRIPTION OF PREFERRED ASPECTS OF THE INVENTION

A disposable cartridge for measuring a property of a sample is described. The disposable cartridge is useful for point-of-care testing (POCT). The disposable cartridge provides for automatic sample volume metering so that after applying an unknown sample volume to the cartridge, a specific volume of the sample is used for measuring the property of the sample.

For example, and as described in detail below, the disposable cartridge may comprise a cartridge body having an upper surface and a lower surface, a cap pivotally connected to the cartridge body by a pin so that the cap is positioned on the upper surface of the cartridge body. The cap comprises a top side and an underside, with the underside comprising a cap recess surrounded by a flat surface. The disposable cartridge further comprises a sample inlet portion located on the upper surface of the cartridge body. The sample inlet portion including:

a sample storage well for storing a first portion of a sample, the sample storage well comprising a top portion for receiving the sample and a bottom portion for releasing a second portion of the sample to a sample storage well conduit;

an air bladder exit port;

a pin hole for receiving the pin, and a sliding surface surrounding the sample storage well and the air bladder exit port, the sliding surface for frictionally engaging the flat surface of the underside of the cap.

The cap includes a sweeping edge that may be used to skim off any excess of the sample when received by the sample storage well, the sample inlet portion or both, when the cap is pivotally rotated from an open position where the cartridge is in an unsealed configuration, to a closed positioned where the cartridge is in a sealed configuration. The sample storage conduit is in fluid communication between the bottom portion of the sample well and a capillary break, and is used to receive the second portion of the sample. The total volume of the sample in the cartridge, when in the sealed configuration, is equivalent to the volume measured from the top portion of the sample storage well to the capillary break. The cartridge body further comprises a detection chamber in fluid communication with the capillary break and the sample storage conduit (via a detection chamber inlet conduit). The detection chamber is for receiving a portion of the total volume of the sample from the sample storage conduit and for generating a signal during sample interrogation, the signal used to calculate a property of the sample. The cartridge body also comprises a vent in fluid communication with the detection chamber, the vent for relieving pressure in the detection chamber, and an air bladder in fluid communication with the air bladder exit port. When the disposable cartridge is in the unsealed configuration, the sample storage well is open and available to receive the sample. When in the sealed configuration and the cap is in a closed position, the cap recess facilitates provision of a closed air passage connecting the air bladder exit port and the sample storage well for communicating pressurized air from the air bladder to the sample storage well via the air bladder exit port, so that when the air bladder is pressed, the volume of the sample, or a portion thereof, is urged from the sample storage conduit into the detection chamber.

Also described herein is a method for measuring a property of a blood sample. The method comprises depositing a blood sample into the sample storage well of the disposable cartridge as defined herein, the disposable cartridge in the unsealed configuration. The cartridge cap is rotated about the pin which skims off excess blood and places the disposable cartridge in the sealed configuration to produce a sealed cartridge that comprises the volume of the sample. The sealed cartridge is inserted into a receptor of an analyzer, the analyzer comprising the receptor for receiving the disposable cartridge, one or more than one processor for controlling the analyzer; means for activating the air bladder; and a detector for receiving the signal from the detection chamber and sending the signal to the one or more than one processor for transforming the signal into the property of the sample. Once inserted into the receptor, the air bladder is activated and provides the pressurized air so that the total volume of the sample moves through one of the detection chamber inlet conduit containing the at least one reagent, and a reagent chamber, containing the at least one reagent, and disposed between an end of the sample storage conduit adjacent to the capillary break, thereby dissolving the at least one reagent into the blood to produce a mixture of the blood and the at least one reagent. The mixture of blood is urged and the at least one reagent into the detection chamber; and the property of the blood sample is measured in the detection chamber using the analyzer.

As used herein, the terms "comprising," "having," "including" and "containing," and grammatical variations thereof, are inclusive or open-ended and do not exclude additional, un-recited elements and/or method steps. The term "consisting essentially of" when used herein in connection with a use or method, denotes that additional elements and/or method steps may be present, but that these additions do not materially affect the manner in which the recited method or use functions. The term "consisting of" when used herein in connection with a use or method, excludes the presence of additional elements and/or method steps. A use or method described herein as comprising certain elements and/or steps may also, in certain embodiments consist essentially of those elements and/or steps, and in other embodiments consist of those elements and/or steps, whether or not these embodiments are specifically referred to. In addition, the use of the singular includes the plural, and "or" means "and/or" unless otherwise stated. The term "plurality" as used herein means more than one, for example, two or more, three or more, four or more, and the like. Unless otherwise defined herein, all technical and scientific terms used herein have the same meaning as commonly understood by one of ordinary skill in the art. As used herein, the term "about" refers to an approximately +/−10% variation from a given value. It is to be understood that such a variation is always included in any given value provided herein, whether or not it is specifically referred to. The use of the word "a" or "an" when used herein in conjunction with the term "comprising" may mean "one," but it is also consistent with the meaning of "one or more," "at least one" and "one or more than one."

Disposable Cartridges with a Rapid Sample Metering System

Detailed description of novel features of examples of the invention is discussed now, and is best understood with reference to the accompanying drawings. These examples are to be considered non-limiting, and a person of ordinary skill in the art will understand that variations are within the scope of the invention, even though they are not explicitly illustrated. The same reference numerals are used for similar elements in different examples; in some cases, letters are appended to the end of the reference numerals to denote the embodiment of the invention illustrated. For example, the letters "b", "c" and "d" are used to refer to the $2^{nd}$, $3^{rd}$ and $4^{th}$ embodiments or examples of the invention respectively. It should be noted that absence of a letter after a reference numeral does not imply that the element belongs to the first example of the invention. For easy reference, Table 1 provides a list of the reference numerals used, and a brief description of the corresponding structural features.

TABLE 1

| Reference Numerals | Description of Structural Features |
|---|---|
| 10 | A first embodiment of a cartridge |
| 10b | A second embodiment of a cartridge |
| 10c | A third embodiment of a cartridge |
| 10d | A fourth embodiment of a cartridge |
| 20 | First housing member of cartridge 10 |
| 20b | First housing member of cartridge 10b |
| 20c | First housing member of cartridge 10c |
| 20d | First housing member of cartridge 10d |
| 30 | Second housing member of cartridge 10 |
| 30b | Second housing member of cartridge 10b |
| 30c | Second housing member of cartridge 10c |
| 30d | Second housing member of cartridge 10d |
| 40 | A sample inlet portion of cartridge 10, which comprises the elements of the cartridge that interact with the cap 50 |
| 40b | A sample inlet portion of cartridge 10b, which comprises the elements of the cartridge that interact with the cap 50b |
| 40c | A sample inlet portion of cartridge 10c, which comprises the elements of the cartridge that interact with the cap 50c |
| 40d | A sample inlet portion of cartridge 10d, which comprises the elements of the cartridge that interact with the cap 50d |
| 41 | A sample storage well of an inlet portion 40 of cartridge 10 |
| 41b | A sample storage well of an inlet portion 40b of cartridge 10b |
| 41d | A sample storage well of an inlet portion 40d of cartridge 10d |
| 43 | Top portion of a sample storage well 41 of cartridge 10 |
| 43b | Top portion of a sample storage well 41b of cartridge 10b |
| 43c | Top portion of a sample storage well of cartridge 10c |
| 43d | Top portion of a sample storage well 41d of cartridge 10d |
| 45 | Bottom portion of sample storage well 41 of cartridge 10 |
| 45b | Bottom portion of sample storage well 41b of cartridge 10b |
| 45d | Bottom portion of sample storage well 41d of cartridge 10d |
| 45c | Bottom portion of sample storage well of cartridge 10c |
| 45d | Bottom portion of sample storage well of cartridge 10d |
| 47 | A sample overflow well of an inlet portion 40 of cartridge 10 |
| 47b | A sample overflow well of an inlet portion 40b of cartridge 10b |
| 48c | Groove disposed at the underside and at the sweeping portion of the cap 50c of cartridge 10c, for storing excess sample |
| 48d | Groove disposed at the underside and at the sweeping portion of the cap 50d, for storing excess sample |
| 49 | A sliding surface of inlet portion 40 of cartridge 10, surrounding sample storage well 41 |
| 49b | A sliding surface of inlet portion 40b of cartridge 10b, surrounding sample storage well 41b |
| 49c | A sliding surface of inlet portion 40c of cartridge 10c, surrounding sample storage well 41c |
| 49d | A sliding surface of inlet portion 40d of cartridge 10d, surrounding sample storage well 41d |
| 50 | A cap for closing inlet portion 40 of cartridge 10 |
| 50b | A cap for closing inlet portion 40b of cartridge 10b |

TABLE 1-continued

| Reference Numerals | Description of Structural Features |
|---|---|
| 50c | A cap for closing inlet portion 40c of cartridge 10c |
| 50d | A cap for closing inlet portion 40d of cartridge 10d |
| 51 | Top side of cap 50 of cartridge 10 |
| 51b | Top side of cap 50b of cartridge 10b |
| 52 | Underside of cap 50 of cartridge 10 |
| 52b | Underside of cap 50b of cartridge 10b |
| 53 | A sweeping portion of cap 50 of cartridge 10 |
| 53b | A sweeping portion of cap 50b of cartridge 10b |
| 53c | A sweeping portion of cap 50c of cartridge 10c |
| 54 | A trailing portion of cap 50 of cartridge 10 |
| 54b | A trailing portion of cap 50b of cartridge 10b |
| 54c | A trailing portion of cap 50c of cartridge 10c |
| 55 | Cap recess in the underside of cap 50 of cartridge 10 |
| 55b | Cap recess in the underside of cap 50b of cartridge 10b |
| 55c | Cap recess in the underside of cap 50c of cartridge 10c |
| 55d | Cap recess in the underside of cap 50d of cartridge 10d |
| 57 | A cap sealing ring/washer (referred to as a gasket in some embodiments) in cap 50 of cartridge 10 |
| 57c | A cap sealing gasket in cap 50c of cartridge 10c |
| 57d | A cap sealing gasket in cap 50d of cartridge 10d |
| 58 | A sweeping cap edge disposed at the sweeping portion 53 of cap 50 for skimming off excess sample |
| 58b | A sweeping cap edge disposed at the sweeping portion 53b of cap 50b for skimming off excess sample |
| 58c | A sweeping cap edge disposed at the sweeping portion 53c of cap 50c for skimming off excess sample |
| 58d | A sweeping cap edge disposed at the sweeping portion of cap 50d for skimming off excess sample |
| 59 | A cap handle for facilitating rotation of cap 50 |
| 60 | A pin for hingedly (or pivotally) attaching the cap 50 to the sample inlet portion 40 and allowing the cap to swing with the cap sealing ring/washer 57 frictionally engaged with the surface 49 (see FIG. 2A) of inlet portion 40. Note: The term pivot is used to describe the pin or shaft 62c used with latch 70c. The attachment mechanism illustrated in FIG. 6F is optionally the same for the two hinged attachments. |
| 60b | A pin in cap 50b for hingedly attaching the cap to the sample inlet portion 40b and allowing the cap to swing with the non-recessed portion of the underside of the cap frictionally engaged with the surface 49b of inlet portion 40b |
| 60c | A pin in cap 50c for hingedly attaching the cap to the sample inlet portion 40c and allowing the cap to swing with the gasket 57 frictionally engaged with the surface 49c of inlet portion 40c |
| 60d | A pin in cap 50d for hingedly attaching the cap to the sample inlet portion 40d and allowing the cap to swing with the gasket 57d frictionally engaged with the surface 49d of inlet portion 40d |
| 61 | A pin hole in first housing member for receiving pin 60 |
| 61b | A pin hole for receiving pin 60b |
| 61c | A pin hole for receiving pin 60c |
| 62c | Pivot of latch 70c |
| 63 | Bottom of pin hole 61 |
| 63b | Bottom of pin hole 61b |
| 63c | Bottom of pin hole 61c |
| 64c | Hole for receiving pivot 62c of latch 70c of cartridge 10c |
| 65b | Snap fit lip in pin 60b for locking pin 60b in pinhole 61b |
| 66c | Bottom of pivot hole 64c |
| 67b | Snap fit lip in pinhole 61b for locking pin 60b in pinhole 61b |
| 70 | Cap latch in inlet portion 40 |
| 70b | Cap latch in inlet portion 40b |
| 70c | Cap latch in inlet portion 40c |
| 71 | Pin hole in cap 50 for receiving pin 60 |
| 72 | Cap stop for keeping cartridge 10d in either an unsealed configuration or a sealed configuration |
| 73 | Cap latch recess in cap latch 70 of cartridge 10 |
| 73b | Cap latch recess in cap latch 70b of cartridge 10b |
| 81 | A sample storage conduit entrance of a cartridge 10 |
| 81b | A sample storage conduit entrance of a cartridge 10b |
| 81c | A sample storage conduit entrance of a cartridge 10c |
| 83 | A sample storage conduit of a cartridge 10 (see FIG. 1G) |
| 83b | A sample storage conduit of a cartridge 10b (see FIG. 5G) |
| 83c | A sample storage conduit of a cartridge 10c (see FIG. 11B) |
| 83d | A sample storage conduit of a cartridge 10c (see FIG. 12D) |
| 84c | Junction of sample storage conduit 83c and capillary break 87c of cartridge 10c (see FIG. 11B) |
| 85 | A sample storage conduit groove of a cartridge 10 |
| 85b | A sample storage conduit groove of a cartridge 10b |
| 85c | A sample storage conduit groove of a cartridge 10c (see FIG. 9H) |
| 87' | Portion of a capillary break in a first housing member of cartridge 10 |
| 87'' | Portion of a capillary break in a second housing member of cartridge 10 |
| 87 | A capillary break of a cartridge, comprising portions 87', 87'', and a gasket cut-out 115 aligned with portions 87' and 87'' |
| 87b' | Portion of a capillary break in a first housing member of cartridge 10b |
| 87b'' | Portion of a capillary break in a second housing member of cartridge 10b |
| 87b | A capillary break of a cartridge, comprising portions 87b', 87b'', and a gasket cut-out 115b aligned with portions 87b' and 87b'' |
| 87c | A capillary break of cartridge 10c (see FIG. 11E) |
| 87c'' | Portion of a capillary break 87c in a second housing member 30c of cartridge 10c |
| 88 | A mixing chamber entrance groove of cartridge 10b (see FIG. 5B) |
| 89 | A mixing chamber of a cartridge 10b (see FIG. 5G) |
| 89c | A mixing chamber of a cartridge 10c |
| 89c' | Portion of mixing chamber 89c in a first housing member 20c of cartridge 10c |
| 89c'' | Portion of mixing chamber 89c in a second housing member 30c of cartridge 10c |
| 91b | A post capillary break conduit for providing fluid communication between the capillary break 87b and the mixing chamber 89 (see FIG. 5G) |
| 91c | A post capillary break conduit for providing fluid communication between the capillary break 87c and the reagent chamber 209c (see FIG. 11B) |
| 92c | Junction of capillary break 87c and post capillary break conduit 91c (see FIG. 11E) |
| 100 | Double-sided sticky gasket of cartridge 10 |
| 100b | Double-sided sticky gasket of cartridge 10b |
| 100c | Double-sided sticky gasket of cartridge 10c |
| 101 | Gasket cut-out 101 positioned to provide fluid connection between the bottom of a sample storage well and a sample storage conduit entrance 81 of cartridge 10 |
| 101b | Gasket cut-out 101b positioned to provide fluid connection between a bottom of a sample storage well and a sample storage conduit entrance of cartridge 10b |
| 101c | Gasket cut-out 101c positioned to provide fluid connection between a bottom of a sample storage well and a sample storage conduit entrance of cartridge 10c |
| 103 | Gasket cut-out 103 positioned to provide fluid connection between an air bladder window and an air bladder cavity |
| 103b | Gasket cut-out 103b positioned to provide fluid connection between air bladder 340b and air bladder duct 343b |
| 105 | Gasket cut-out 105 positioned to provide fluid connection between an air bladder and an air bladder exit port 344 |
| 105b | Gasket cut-out 105 positioned to provide fluid connection between an air bladder duct 343b and an air bladder exit port 344b |
| 107 | Gasket cut-out 107 is an extension of cut out 103, positioned to provide fluid connection between air bladder 340 (see FIG. 3A) and air bladder exit port 344b |
| 109 | Gasket cut-out 109 position to align with pin hole 61 |
| 109b | Gasket cut-out 109b position to align with pin hole 61b |
| 109c | Gasket cut-out 109c position to align with pin hole 61c |
| 115 | Gasket cut-out 115 position to align with capillary break 87 |
| 115b | Gasket cut-out 115b position to align with capillary break 87b |
| 115c | Gasket cut-out 115c position to align with capillary break 87c of cartridge 10c |
| 117 | Gasket cut-out 117 positioned to provide fluid connection between an optical chamber inlet conduit 217 (see FIG. |

TABLE 1-continued

| Reference Numerals | Description of Structural Features |
|---|---|
| | 1G) and an optical chamber overflow conduit 227, and positioned to align with optical windows 213 and 215; in cartridge 10, gasket cut-out 117 defines an optical chamber 211 (see FIG. 1H). |
| 117c | Gasket cut-out 117c positioned to provide fluid connection between an optical chamber inlet conduit 217c and an optical chamber overflow conduit 227c, and positioned to align with optical windows 213c and 215c |
| 119 | Gasket cut-out 119 positioned to provide fluid connection between the optical chamber overflow conduit 227 and a waste receptacle 231 of cartridge 10 (see FIG. 1H) |
| 119b | Gasket cut-out 119b positioned to provide fluid connection between the distal end of the biosensor conduit 337 and a waste receptacle cavity 231b of cartridge 10b |
| 121 | Gasket cut-out 121 positioned to align with a portion of the biosensor conduit groove 335 and the active area 323 of the biosensor array 330 of cartridge 10b |
| 123 | Gasket cut-out 123 positioned to align with a portion of the inlet of the mixing chamber 89 of cartridge 10b (see FIG. 5G) |
| 125 | Gasket cut-out 125 positioned to align with a portion of the outlet of the mixing chamber 89 of cartridge 10b (see FIG. 5G) |
| 127 | Gasket cut-out 127 positioned to align with the reagent chamber 209c of cartridge 10c (see FIG. 118) |
| 129 | Gasket cut-out 129 positioned to align with the mixing chamber 89c of cartridge 10c (see FIG. 118) |
| 133 | Gasket cut-out 133 position to align with latch pivot hole 64c of cartridge 10c |
| 209c | A reagent chamber of cartridge 10c (see FIG. 118) |
| 210c | Conduit for fluidly connecting reagent chamber 209c and mixing chamber 89c (see FIG. 118) |
| 211 | An optical chamber in cartridge 10 for receiving sample mixed with reagent, and positioned to align with at least a portion of an optical window (see FIG. 1H) |
| 211c | An optical chamber in cartridge 10c for receiving sample mixed with reagent, and positioned to align with at least a portion of an optical window (see FIG. 11C) |
| 213 | A first optical window of cartridge 10 |
| 213c | A first optical window of cartridge 10c |
| 215 | A second optical window of cartridge 10 |
| 215c | A second optical window of cartridge 10c |
| 217 | Detection chamber Inlet conduit joining capillary break 87 to detection (optical) chamber 211 |
| 217b | Detection chamber Inlet conduit joining mixing chamber 89 to detection chamber (biosensor conduit 337) |
| 217c | Detection chamber Inlet conduit joining mixing chamber 89c and detection (optical) chamber 211c of cartridge 10c |
| 219 | Optical chamber inlet conduit groove of optical chamber inlet conduit 217 of cartridge 10 |
| 226c | Overflow conduit groove of overflow conduit of optical chamber 211c of cartridge 10c |
| 227 | Overflow conduit of optical chamber 211 of cartridge 10 |
| 227c | Overflow conduit of optical chamber 211c of cartridge 10c |
| 229 | Overflow conduit groove of optical chamber 211 of cartridge 10 |
| 231 | A waste receptacle cavity of cartridge 10 |
| 231b | A waste receptacle cavity of cartridge 10b |
| 233 | A waste receptacle vent of cartridge 10 |
| 233b | A waste receptacle vent of a cartridge of cartridge 10b |
| 233c | A vent for the optical chamber overflow conduit 227c of cartridge 10c |
| 237c | Crown of cap knob of cap 50c of cartridge 10c |
| 239c | Neck of cap knob of cap 50c of cartridge 10c |
| 241c | Notch in cap 50c for mating with pivot 62c of latch 70c, when cartridge 10c is in a sealed configuration |
| 321 | Biosensor substrate for printing elements of the biosensors and for facilitating thermal contact with an analyzer heating element (see FIG. 5A) |
| 323 | Active area of a biosensor array 330 of cartridge 10b |
| 325 | Biosensor electrical contact of biosensors (see FIG. 5E) |
| 327 | A biosensor receptacle for arranging one or more biosensors in a cartridge in the form of a cut-out ledge in the second housing member 30b, and for exposing the underside of the biosensor(s) to facilitate heating (see FIG. 5A) |
| 330 | A biosensor array of cartridge 10b |
| 333 | Proximal end of a biosensor conduit groove of cartridge 10b |
| 335 | Distal end of a biosensor conduit groove of cartridge 10b |
| 337 | A biosensor conduit of cartridge 10b (see FIG. 5G) |
| 340 | An air bladder of cartridge 10 |
| 340b | An air bladder of cartridge 10b |
| 341 | An air bladder window of an air bladder 340 |
| 341b | An air bladder window of an air bladder 340b |
| 342 | A groove in member 30b for defining air bladder duct 343b |
| 343b | An air bladder duct for providing fluid connection between an air bladder 340b and an air bladder exit port 344b |
| 344 | An air bladder exit port of a sample inlet portion 40 of cartridge 10 |
| 344b | An air bladder exit port of a sample inlet portion 40b of cartridge 10b |
| 344c | An air bladder exit port of a sample inlet portion 40c of cartridge 10c |
| 345 | Flexible member of a cartridge for covering air bladder window 341 of cartridge 10 for facilitating operation of the air bladder 340 |
| 345b | Flexible member of a cartridge for covering air bladder window 341b of cartridge 10b for facilitating operation of the air bladder 340b |
| 345c | Flexible member of a cartridge for covering air bladder window 341c of cartridge 10c for facilitating operation of the air bladder 340c |
| 346c | Air bladder duct for providing fluid connection between an air bladder 340c and an air bladder exit port 344c (see FIG. 11E) |
| 347 | Recess for nesting flexible member 345, disposed at the surface of first housing member 20 of cartridge 10 |
| 347b | Recess for nesting flexible member 345b, disposed at the surface of first housing member 20b of cartridge 10b |
| 351c | Bottom cover for covering sample storage conduit 83c of cartridge 10c |

Shown in FIG. 1A is an exploded view of an example of a disposable cartridge 10 for measuring a property of a sample, the cartridge having a rapid sample metering system. From top to bottom, the components are described. Pin 60 is used to hingedly (pivotally) attach cap 50 to the cartridge, via pin hole 61 shown in the first housing member 20; the bottom of the pin hole 61 is shown as 63 in the second housing member 30. Flexible member 345 nests in a recess 347 in the first housing member 20 and is used to seal off the air bladder window 341. An optional cap, sealing ring, or washer 57, may be attached to the underside of the cap 50. In some embodiments, the sealing ring/washer is referred to as a gasket, which may be made from several different material known to a person skilled in the art. PTFE (Polytetrafluoroethylene, also known as Teflon®) is a good example of gasket material. An advantage of PTFE in this application is that it has a very low surface energy and can pass easily over sliding surface 49 of inlet portion 40, without dragging the blood sample as the seal 57 moves along the surface of inlet portion 40.

Also shown in the first housing member 20 is the first optical window 213, an air bladder exit port 344, the top portion 43 of a sample storage well 41 (see FIG. 1G), a cap latch 70, and the sample inlet portion 40. Sample inlet portion 40 comprises sample storage well 43, air bladder exit port 344, pin hole 61, and sliding surface 49 that surrounds the top portion of the sample storage well 43 and the air bladder exit port 344. Elements 40, 344, 43, 70 of cartridge 10 interact with the cap 50 as described in more detail below. Some embodiments of the cartridge described herein provide a good seal between the cap 50 and the sample inlet portion 40, without a cap latch 70, depending on the robustness of the hinged attachment of the cap. For example the fourth embodiment (cartridge 10*d*; see FIGS. 12A-12D) is an example of a cartridge without a cap latch. An advantage to having a robust hinged, or pivotal, attachment and no cap latch is the greater space provided at the sample storage well 41, for accommodating the heel of a baby or a large adult finger.

Still referring to FIG. 1A, there is shown a double-sided sticky gasket 100, comprising several gasket cut-outs, including:

cut-out 101, positioned to provide fluid connection between the bottom of a sample storage well and a sample storage conduit entrance 81 of cartridge 10;

cut-out 109 position to align with pin hole 61;

cut-outs 105, 107 and 103 are positioned to provide fluid connection between an air bladder cavity 340 (FIG. 3A) and air bladder exit port 344;

cut-out 115 position to align with capillary break 87;

cut-out 117 positioned to provide fluid connection between an optical chamber inlet conduit 217 (see FIG. 1G) and an optical chamber overflow conduit 227 (FIG. 1H), and positioned to align with optical windows 213 and 215 (FIG. 1H); in cartridge 10;

cut-out 117 defines an optical chamber 211 (see FIG. 1H);

cut-out 119 positioned to provide fluid connection between the optical chamber overflow conduit 227 (FIG. 1H) and a waste receptacle 231 of cartridge 10.

Below gasket 100 is the second housing member 30, showing the following elements: a sample storage conduit entrance 81; a sample storage conduit groove 85 that defines the sample storage conduit 83 (FIG. 1G); the second portion 87″ of capillary break 87 (see FIG. 1F); and a waste receptacle cavity 231.

The assembled cartridge body, comprising the first housing member 20, the sticky gasket 100, and the second housing member 30 may be made of a clear polymeric material, a clear plastic, a material that is transparent to a wavelength of electromagnetic radiation used to interrogate the sample, or a combination thereof.

Shown in FIG. 1B is a bottom view of the first housing member 20 of the cartridge shown in FIG. 1A showing the optical inlet conduit groove 219 that defines the optical chamber inlet conduit 217 when housing member 20 is attached to sticky gasket 100. Optical chamber inlet conduit 217 joins in fluid communication, the capillary break 87 with the first optical window 213. Overflow conduit groove 229 defines the overflow conduit 227 (when housing member 20 is attached to sticky gasket 100) that joins the first optical window 213 with the waste receptacle cavity 231 in the assemble cartridge. Also shown in FIG. 1B is bottom portion 45 of sample storage well 41, pin hole 61 and air bladder exit port 344. Shown in FIG. 1C is the bottom view of the first housing member 20 shown in FIG. 1B, overlaid by, and in alignment with, gasket 100 shown in FIG. 1A. Shown in FIG. 1D is a top view of the second housing member 30 of the cartridge shown in FIG. 1A. Shown in FIG. 1E is a top view of the second housing member 30 shown in FIG. 1D, overlaid by, and in alignment with, the gasket 100 shown in FIG. 1A.

Shown in FIG. 1F is a top view of the cartridge 10 shown in FIG. 1A, with the cap 50 in a fully closed position. Illustrated in FIG. 1G is an enlarged cross-sectional view through the cartridge shown in FIG. 1F along line G-G, showing the sample storage well 41, the sample storage conduit entrance 81, the sample storage conduit 83, the sections 87′ and 87″ of the capillary break 87 (see hidden view in FIG. 1F), and Inlet conduit 217 of optical chamber 211 (see FIG. 1H). Cap handle 59 is also indicated. Shown in FIG. 1H is a second enlarged cross-sectional view through the cartridge shown in FIG. 1F along line H-H, showing, an optical chamber 211 (defined by cut-out 117 of the double-sided sticky gasket 100), a first optical window 213, a second optical window 215, an optical chamber overflow conduit 227, a waste receptacle 231 and its vent 233. The optical chamber 211 is a non-limiting example of a detection chamber. Shown in FIG. 1J is a third cross-sectional view through the cartridge shown in FIG. 1F along line J-J, showing the sample storage conduit entrance 81, mating with the bottom portion 45 of the sample storage well 41. This mating aspect is better illustrated in FIG. 5H, regarding cartridge 10*b*

Shown in FIG. 2A is a top view of the cartridge 10 shown collectively in FIGS. 1A-1J, with the cap 50 and pin 60 removed to indicate the arrangement of components 61 (pin hole for receiving pin 60), 344 (air bladder exit port of sample inlet portion 40), 43 (top portion of sample stage well 41) and 47 (sample overflow well of sample inlet portion 40). Shown in FIG. 2B is a top view of the cartridge 10 shown collectively in FIGS. 1A-1J, with the cap 50 in a position for an unsealed configuration of the cartridge. In the unsealed configuration the cap 70 may rest against cap latch 70 as shown in FIG. 2A, and the cap latch may act as a cap stop to define the unsealed configuration.

Figure 2C:
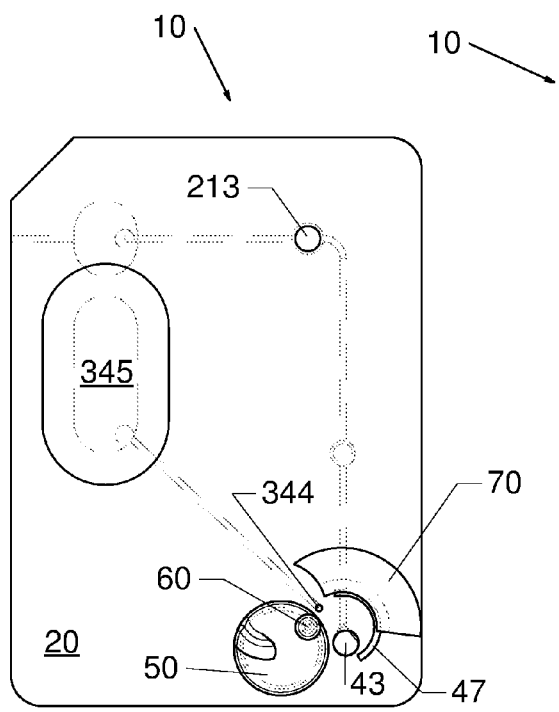
FIG. 2C is a top view of the cartridge 10 shown collectively in FIGS. 1A-1J, with the cap 50 in a partly open position.
Figure 2D:
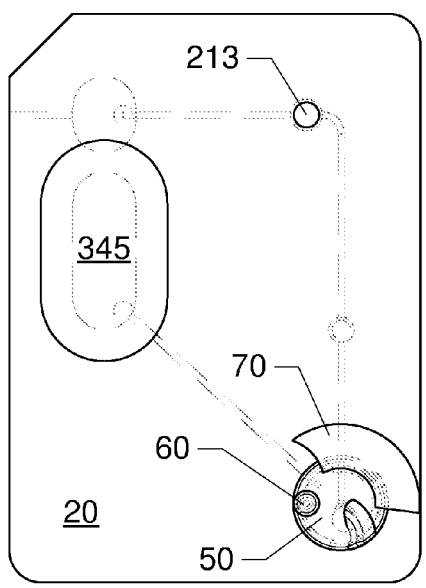
FIG. 2D is a top view of the cartridge 10 shown collectively in FIGS. 1A-1J, with the cap 50 in a fully closed position

Shown in FIG. 2C is a top view of the cartridge 10 shown collectively in FIGS. 1A-1J, with the cap 50 in a position for a partly open configuration of the cartridge. Shown in FIG. 2D is a top view of the cartridge 10 shown collectively in FIGS. 1A-1J, with the cap 50 in a position for a sealed configuration of the cartridge. FIGS. 2B-2D illustrate how, by moving the position of cap 50, the cartridge is adjustable between an unsealed and a sealed configuration. In the sealed configuration shown in FIG. 2D, the cap 70 is registered with cap latch 70 and the cap latch is acting as a cap stop to define the sealed configuration.

Referring to FIGS. 3A-3D are perspective views of the cartridge 10 shown in FIGS. 2A & 2D, providing more details of the sample inlet portion 40 and its association with the cap 50. Shown in FIG. 3A is a top perspective view of the cartridge 10 shown in FIG. 2A, with air bladder 340 open. Shown in FIG. 3B is a detailed view of detail B of the cartridge shown in FIG. 3A, and indicates the arrangement of components 344, 61, 43, 47, and the cap latch recess 73 of cap latch 70. Shown in FIG. 3C is a top perspective view of the cartridge 10 with cap 50 positioned over sample inlet portion 40 so that the cartridge is in a sealed configuration. Shown in FIG. 3D is a detailed view of detail D of the cartridge shown in FIG. 3C. An outer periphery of cap 50 is shown to be engaged with cap latch recess 73 of cap latch 70. In this example, the cap latch recess 73 is operating as a latch to retain cap 50 in a closed position where the cartridge is in a sealed configuration. Also shown in FIG. 3D is cap handle 59, that is used to move cap 50 pivotally about pin 60

Figure 4A:
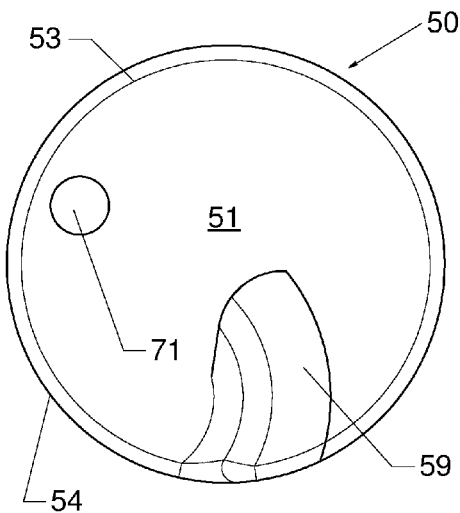
FIG. 4A is a top view of the cap 50 shown in FIGS. 2B-2D.
Figure 4B:
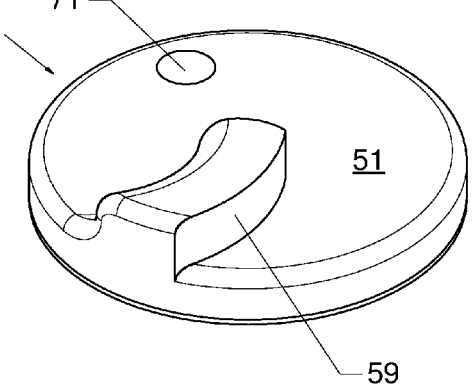
FIG. 4B is a perspective top view of the cap 50 shown in FIG. 4A.
Figure 4C:
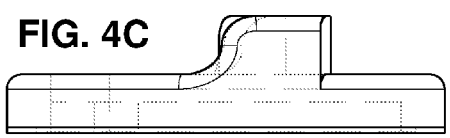
FIG. 4C is a front view of the cap 50 shown in FIG. 4A.
Figure 4D:
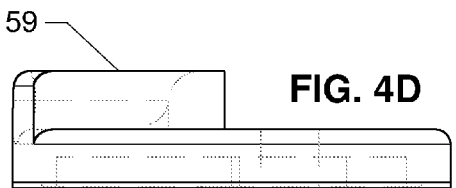
FIG. 4D is a right side view of the cap 50 shown in FIG. 4A.
Figure 4E:
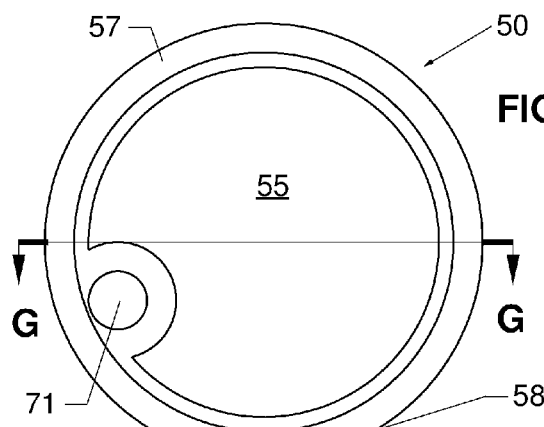
FIG. 4E is a bottom view of the cap 50 shown in FIG. 4A.
Figure 4F:
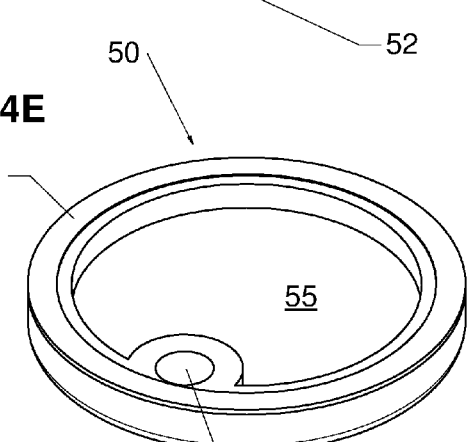
FIG. 4F is a perspective bottom view of the cap 50 shown in FIG. 4E.
Figure 4G:
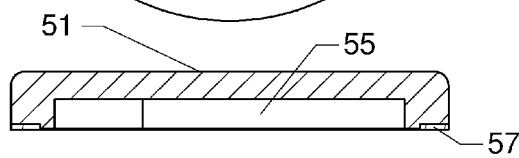
FIG. 4G is a cross-sectional view through the cap 50 shown in FIG. 4E along line G-G.

The details of the cap 50 are illustrated in FIGS. 4A-4G. Shown in FIG. 4A is a top view of the cap 50 shown in FIG. 3D, showing pin hole 71 in cap 50 for receiving pin 60, and the top side 51 of the cap 50, and a cap handle 59 for facilitating rotation of cap 50. Also shown are a sweeping portion 53 of cap 50 and trailing portion 54 of cap 50, in the context of a counterclockwise rotation of the cap 50 about the pin 60, when the cartridge is adjusted from an unsealed configuration (see FIG. 2B) to a sealed configuration (see FIG. 2D). Shown in FIG. 4B is a top perspective view of the cap 50 shown in FIG. 4A. Shown in FIG. 4C is a front view of the cap 50 shown in FIG. 4A. Shown in FIG. 4D is a right side view of the cap 50 shown in FIG. 4A, indicating the underside 52 of cap 50. Shown in FIG. 4E is a bottom view of the cap 50 shown in FIG. 4A, showing a sweeping cap edge 58 disposed at the sweeping portion 53 of cap 50 for skimming off excess sample, and the cap recess 55. A flat surface surrounds the cap recess 55, the flat surface may comprise, for example, a sealing ring 57. In this example, the sweeping cap edge 58 is the edge of the cap sealing ring 57. Shown in FIG. 4F is a bottom perspective view of the cap 50 shown in FIG. 4E. Shown in FIG. 4G is a cross-sectional view through the cap 50 shown in FIG. 4E along line G-G, showing the top side 51 of cap 50, the cap recess 55, and the cap sealing ring 57.

Shown in FIG. 5A is an exploded view of the disposable cartridge 10b for measuring a property of a sample, the cartridge having a rapid sample metering system, according to a second embodiment of the cartridge. This embodiment is similar to the first embodiment of the cartridge 10, and illustrated collectively in FIG. 1A to FIG. 4G, and accordingly, elements common to them share common reference numerals. For some elements, the letter "b" is appended to the end of the reference numerals, in order to indicate that the elements are part of the second embodiment of the cartridge. A first difference between the first (10) and second (10b) embodiments of the cartridge is shape of the cap 50 is circular and the shape of cap 50b is elliptical. It should be understood that these are preferred embodiments, and the shape is not limited to being circular or elliptical. Another non-limiting example is an oval shape that is not elliptical. An advantage of an ellipse, having a major radius and a minor radius, is that it is equivalent to a circle having a radius equal to the major radius of the ellipse, in the context of space between the latch 70b and the pin hole 61b, whereby the pin hole 61b is located at one end of the major axis of the ellipse. The larger space, illustrated in FIG. 6B (compare with illustration in FIG. 2B), is useful for accommodating larger fingers, if blood is obtained from a finger prick. A second difference is that the pin 60b is an integral part of the cap 50b, as illustrated collectively in FIGS. 8A-8G. A third difference is that cartridge 10b comprises a mixing chamber 89, for mixing sample and one or more reagent. A fourth difference is that the detection system in the first embodiment of the cartridge is optical or spectrophotometric, whereas the detection system in the second embodiment is electrochemical or biosensors. A person of ordinary skill will appreciate that other embodiments of the cartridge can have either, both of the aforementioned detection systems, or some other detection system. The other minor differences will become obvious by following the reference numerals and the corresponding description of structural features provided in Table 1.

Shown in FIG. 5B is a bottom view of the first housing member 20b of the cartridge shown in FIG. 5A. Shown in FIG. 5C is the bottom view of the first housing member 20b shown in FIG. 5B, overlaid by and in alignment with the gasket 100b shown in FIG. 5A. Shown in FIG. 5D is a top view of the second housing member 30b of the cartridge shown in FIG. 5A. Shown in FIG. 5E is the top view of the second housing member 30b shown in FIG. 5D, overlaid by and in alignment with the gasket 100b shown in FIG. 5A.

Figure 5F:
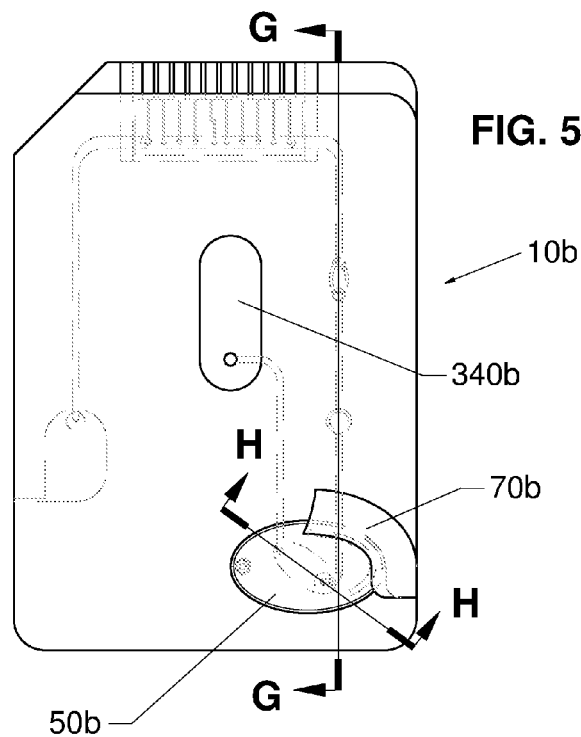
FIG. 5F is a top view of the cartridge 10b shown in FIG. 5A, with the cap 50b in a fully closed position, and air bladder 340b open.
Figure 5G:
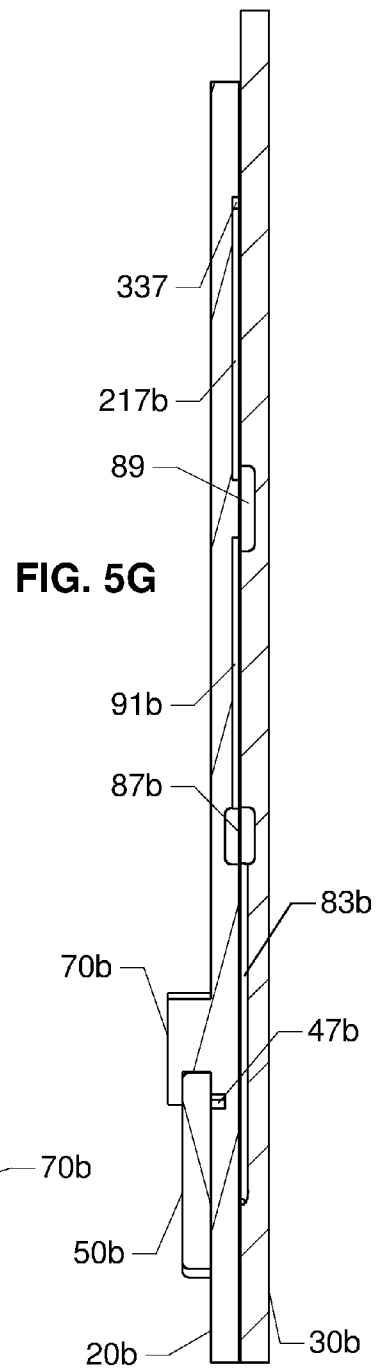
FIG. 5G is an enlarged first cross-sectional view through the cartridge 10b shown in FIG. 5F along line G-G.
Figure 5H:
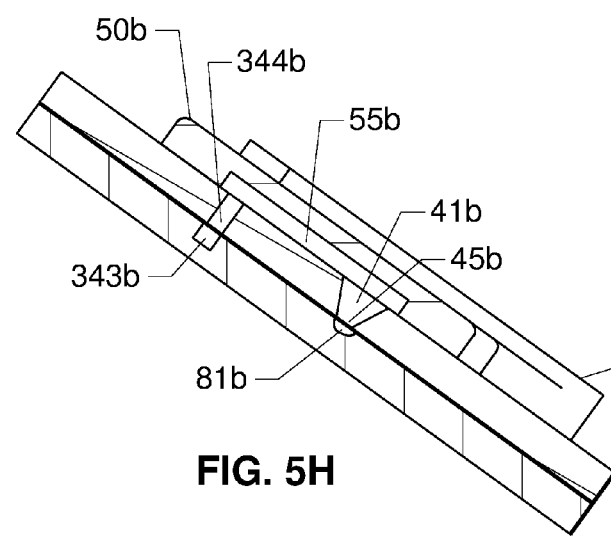
FIG. 5H is an enlarged second cross-sectional view through the cartridge 10b shown in FIG. 5F along line H-H.

Shown in FIG. 5F is a top view of the cartridge 10b shown in FIG. 5A, with the cartridge in a sealed configuration, and with the air bladder laminate hidden, in order to view the air bladder 340b. Shown in FIG. 5G is an enlarged first cross-sectional view through the cartridge 10b shown in FIG. 5F along line G-G. Shown in FIG. 5H is an enlarged second cross-sectional view through the cartridge 10b shown in FIG. 5F along line H-H, illustrating the fluid connection between the air bladder duct 343b and the sample well 41b, via the air bladder exit port 344b, and the cap recess 55b. The arrangement of the bottom 45b of the sample storage well 41b with the sample storage conduit entrance 81b, is also illustrated.

Figure 6A:
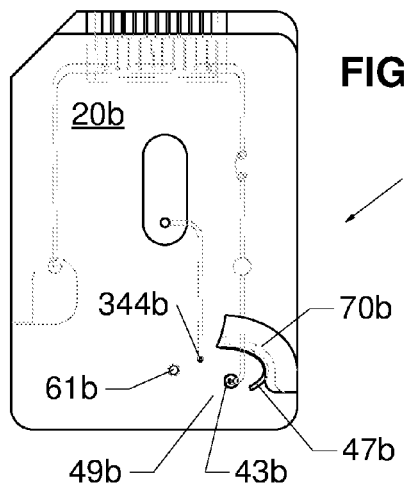
FIG. 6A is a top view of the cartridge 10b shown collectively in FIGS. 5A-5H, with the cap 50b removed
Figure 6B:
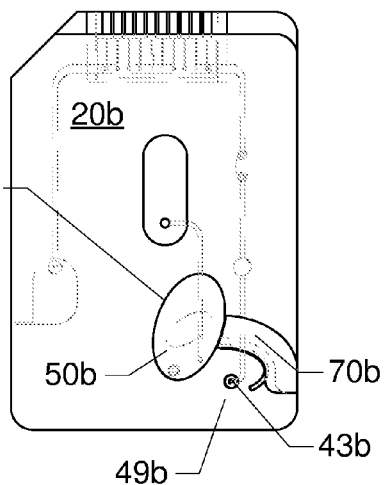
FIG. 6B is a top view of the cartridge 10b shown collectively in FIGS. 5A-5H, with the cap 50b in a fully open position.
Figure 6C:
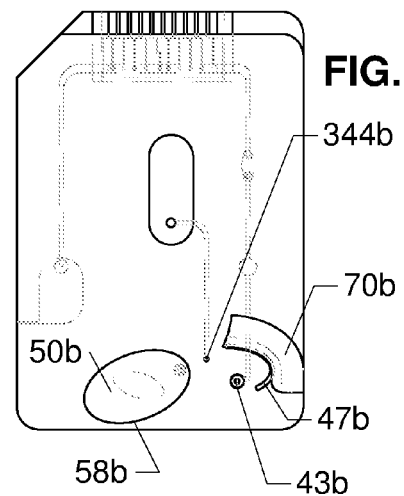
FIG. 6C is a top view of the cartridge 10b shown collectively in FIGS. 5A-5H, with the cap 50b in a partly open position.
Figure 6D:
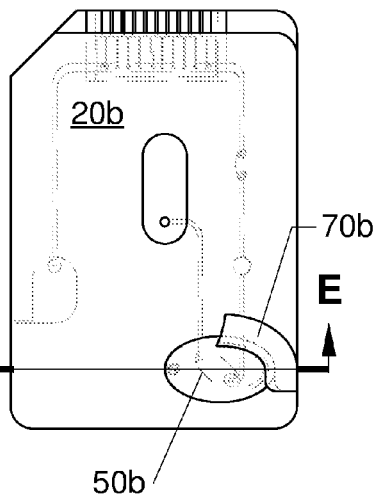
FIG. 6D is a top view of the cartridge 10b shown collectively in FIGS. 5A-5H, with the cap 50b in a fully closed position.
Figure 6F:
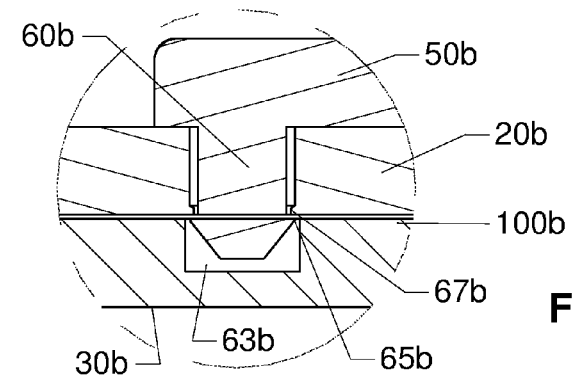
FIG. 6F is a detailed view of detail F of cartridge 10b shown in FIG. 6E, showing a snap-fit mechanism for attaching the pin 60b of cap 50b in the cartridge.
Figure 6E:
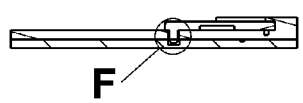
FIG. 6E is a cross-sectional view of cartridge 10b shown in FIG. 6D along line E-E.

Shown in FIG. 6A is a top view of the cartridge 10b shown collectively in FIGS. 5A-5H, with the cap 50b hidden. Shown in FIG. 6B is a top view of the cartridge 10b shown collectively in FIGS. 5A-5H, with the cartridge in an unsealed configuration. Shown in FIG. 6C is a top view of the cartridge 10b shown in FIG. 6B, with the cap 50b in a partially open position. Shown in FIG. 6D is a top view of the cartridge 10b shown collectively in FIGS. 6B-6C, with the cartridge in a sealed configuration. Shown in FIG. 6E is a cross-sectional view of cartridge 10b shown in FIG. 6D along line E-E. Shown in FIG. 6F is a detailed view of detail F of cartridge 10b shown in FIG. 6E, showing a snap-fit mechanism for engaging the cap 50b in the cartridge 10b shown collectively in FIGS. 6B-6D. Description of the structural features is provided in Table 1.

Shown in FIG. 7A is a perspective view of the cartridge 10b shown in FIG. 6A. Shown in FIG. 7B is a detailed view of detail B of the cartridge shown in FIG. 7A, showing details of the sample inlet portion 40b. Shown in FIG. 7C is a perspective view of the cartridge 10b shown in FIG. 6D. Shown in FIG. 7D is a detailed view of detail D of the cartridge shown in FIG. 7C. Description of the structural features is provided in Table 1.

Shown in FIG. 8A is a top view of the cap 50b shown in FIGS. 7C-7D, showing a sweeping portion 53b of cap 50b and trailing portion 54b of cap 50b, in the context of counterclockwise rotation of the cap 50b about the pin 60b, when the cartridge is adjusted from an unsealed configuration (see FIG. 6B) to a sealed configuration (see FIG. 6D). Shown in FIG. 8B is a perspective view of the cap 50b shown in FIG. 8A. Shown in FIG. 8C is a front view of the cap 50b shown in FIG. 8A, showing the top side 51b, the underside 52b, the pin 60b and a snap fit lip 65b for locking pin 60b in pinhole 61b. Shown in FIG. 8D is a right side view of the cap 50b shown in FIG. 8A. Shown in FIG. 8E is a bottom view of the cap 50b shown in FIG. 8A, showing a sweeping cap edge 58b disposed at the sweeping portion 53b of cap 50 for skimming off excess sample, and the cap recess 55b. In this embodiment of cap 50b, there is no gasket and the cap is made of suitable material that can provide a sealed configuration of the cartridge. Shown in FIG. 8F is a perspective view of the cap 50b shown in FIG. 8E. Shown in FIG. 8G is a cross-sectional view through the cap 50b shown in FIG. 8E along line G-G, showing the cap recess 55b and the pin snap fit lip 65b. The means provided for hingedly attaching the cap are examples only, and other means for hingedly attaching the cap to the rest of the cartridge are considered to be within the scope of the invention.

Sample Measurement (Using Cartridge 10b as a Non-Limiting Example)

Measurement of any property of a liquid sample, for example glucose concentration or prothrombin time, can be considered as non-limiting examples for illustrating the use of the cartridge. In this illustration, cartridge 10b will be used (see FIGS. 5A to 8G). In general terms, the present disclosure provides a disposable cartridge for metering a sample for measuring a property of the sample, the cartridge comprising:

1) a housing comprising a first housing member 20*b* and a second housing member 30*b*, bonded together by a double-sided sticky gasket 100*b*;

2) a cap 50*b* having a top side 51*b*, an underside 52*b*, a sweeping cap edge 58*b* for skimming off excess sample, and a cap recess 55*b* in the underside of the cap for creating a closed air passage illustrated in FIG. 5H;

3) a pin 60*b* for hingedly, or pivotally, attaching the cap 50*b* to an inlet portion 40*b* of the cartridge via pin hole 61*b*. The sample inlet portion 40*b*, comprises elements of the cartridge that interact with the cap 50*b* and comprises:

a) the top 43*b* of a sample storage well 41*b* for receiving the sample;

b) the sample storage well 41*b* for storing a portion of the sample;

c) a sliding surface 49*b* (see FIG. 6A) for frictionally engaging the cap 50*b*;

d) a hole 61*b* for receiving the pin 60*b* for hingedly attaching the cap 50*b* to the sample inlet portion 40*b*;

e) a sample overflow well 47*b* for receiving the excess sample during the period of closing the cap 50*b*; In some examples of the cartridge, for example, cartridges 10*c* and 10*d*, the sample overflow well 47*b* is optional. For example, with respect to cartridge 10*c*, the sweeping portion 53*c* of the cap 50*c* (see FIG. 10A) comprises a groove 48*c* (see FIG. 10F) disposed in the underside of the cap in front of the sweeping edge 58*c*, for holding any excess sample;

f) a cap latch 70*b*, for facilitating a sealed configuration of the cartridge when an outer periphery of cap 50*b* is engaged with cap latch recess 73*b*; and g) an air bladder exit port 344*b* in fluid communication with an air bladder 340*b*.

4) the air bladder 340*b* for providing pressurized air to the air bladder exit port 344*b*;

5) a capillary break 87*b* (see FIG. 5G) for stopping sample flow, the flow being facilitated by capillary action;

6) a post capillary break conduit 91*b* (see FIG. 5G) providing fluid communication between the capillary break 87*b* and a mixing chamber 89;

7) a detection chamber (a conduit 337 over the active area 323; see FIGS. 5A and 5E) of one or more biosensor of a biosensor array 330; in the case of cartridge 10, the detection chamber is the optical chamber 211 (see FIG. 1H) for generating a signal used to determine or calculate a property of the sample;

8) a waste receptacle cavity 231*b* for receiving fluid flowing beyond the detection chamber via distal end of biosensor conduit groove 335; and 9) a vent 233*b* for relieving pressure in the waste receptacle cavity 231*b* (see FIG. 5A).

The cartridge may be pre-loaded with one or more dry reagents deposited at one or more points before the detection chamber 323 (FIG. 5E; or before the optical window defined by 213/211/215, FIG. 1H; or 213*c*/211*c*/215*c*, FIG. 11C). Cartridge 10*b* comprises an optional mixing chamber 89, and a post capillary break conduit 91*b*, which defines the conduit between the capillary break 87*b* and the mixing chamber 89, illustrated in FIG. 5G. In some cartridge embodiments, the one or more reagent is deposited in the mixing chamber 89. Dry thromboplastin is an example of a reagent, which is used for measuring prothrombin time (PT) usually reported as PT-INR (PT-International Normalized Ratio), and dry celite or kaolin are examples of a reagent used for measuring activated clotting time (ACT).

The cartridge is adjustable between an unsealed configuration and a sealed configuration. In the unsealed configuration illustrated in FIG. 6B, the top portion 43*b* of sample storage well 41*b* is configured to receive the sample, and the air bladder exit port 344*b* is covered by the cap 50*b*. In the sealed configuration illustrated in FIGS. 5F & 5H, the cap recess 55*b* facilitates provision of a closed air passage connecting the air bladder exit port 344*b* and the sample storage well 41*b* for transferring pressurized air from the air bladder exit port 344*b* to the sample storage well 41*b*. As the cartridge is adjusted from the unsealed configuration to the sealed configuration (an intermediate configuration is illustrated in FIG. 6C), the sweeping cap edge 58*b* skims off excess sample above the top portion 43*b* (see FIG. 6C in conjunction with FIG. 5H) of the sample storage well 41*b*. The volume of sample in the cartridge in the sealed configuration is equivalent to the volume measured from the top portion 43*b* of the sample storage well 41*b* to the capillary break 87*b* (FIG. 5G). The sample storage well 41*b* also comprises a bottom 45*b* of the sample storage well 41*b*. In this example, the top 43*b* is substantially larger than the bottom 45*b*, as illustrated in FIG. 5H. Having a larger top 43*b* may assist in transferring a drop of blood from a body part, for example a finger, to the sample storage well 41*b*. In the case of a small infant, a heel is a preferred body part. The size of the smaller bottom 45*b* is preferably similar to the size of the sample storage conduit entrance 81*b*, for facilitating blood flow by capillary action.

Once the cartridge is in the sealed configuration, the cartridge is ready to be inserted into a slot or receptor of an analyzer. The analyzer detection system comprises one or more of, optical, spectrophotometric, fluorescence, chemiluminescence, electrochemical, biosensor, amperometric, potentiometric or conductimetric technology. However, these are just examples and other detection systems are considered to be within the scope of the present invention. These detection systems are known to a person skilled in the art and for the sake of brevity, will not be discussed here.

In the case of spectrophotometric or optical measurement, an embodiment of an analyzer comprises a source of electromagnetic radiation (EMR) and one or more photodetectors for measuring the EMR reflected from the optical chamber or transmitted through the optical chamber. In some embodiments of the analyzer, more than one photodetector are arranged as a linear diode array in a spectrometer, the spectrometer also comprising a transmission or reflection grating for dispersing the reflected EMR or transmitted EMR, into component wavelengths. Therefore, the analyzer optionally provides optical measurement at one or more than one wavelength.

Another feature of the cartridge is the flexible member 345*b* of the cartridge 10*b*. This flexible member 345 may be depressed to generate pressurized air for mixing the sample with one or more dry reagent, and for advancing the sample towards the detection chamber. This is facilitated by the fluid connection between an air bladder exit port 344*b* and a sample well 41*b*, via a cap recess 55*b*, illustrated in FIG. 5H. The flexible member can also be repeatedly depressed and released causing the blood to move forward and backward, in order to dissolve the one or more dry reagent in the blood sample, and provide better mixing of sample and reagent.

A method for measuring a property of a blood sample comprises some or all of the following steps, not necessarily in the sequence given. One step is providing a cartridge (for example, one shown as 10*b*) and an analyzer comprising a slot or receptor for receiving a cartridge, the cartridge comprising one or more dry reagent deposited at one or more points before the detection chamber. Cartridge 10b comprises an optional mixing chamber 89, and a post capillary break conduit 91b, which defines the conduit between the capillary break 87b and the mixing chamber 89, illustrated in FIG. 5G. In some cartridge embodiments, the one or more reagent is deposited in the mixing chamber 89. Dry thromboplastin is an example of a reagent, which is used for measuring prothrombin time (PT) usually reported as PT-INR (PT-International Normalized Ratio), and dry celite or kaolin are examples of a reagent used for measuring activated clotting time (ACT).

In another step, the cartridge is placed flat on a table, and the cap 50b is rotated in a clockwise direction until the cap 50b hits the latch 70b, adjusting the cartridge 10b to the unsealed configuration, as illustrated in FIG. 6B. It should be noted that in the fully unsealed configuration, the cap 50b creates maximum opening of the top 43b of the sample storage well 41b, and at the same time, the cap 50b covers the air bladder exit port 344b, thereby mitigating flow of blood into the air bladder exit port 344b.

In another step, a blood sample is allowed to touch the top portion 43b of the sample storage well 41b. The blood is drawn into the sample storage well 41b and into the sample storage conduit 83b, up to the capillary break 87b (see FIG. 5G). Slightly excess blood is applied so that the blood sample bulges above the top portion 43b of the sample storage well 41b. For example, a finger of the patient may be pricked, and after a drop of blood is allowed to develop on the finger, following best practice procedures, a sample of the blood is introduced to the top portion 43b as described above.

In another step, the cap 50b is rotated counterclockwise into the recess 73b of the cap latch 70b, as illustrated in FIG. 6D. Details of the sample inlet portion 40b and its association with cap 50b are illustrated collectively in FIGS. 7A-7D. During the cap movement, the sweeping cap edge 58b skims off excess blood, which is dumped into the sample overflow well 47b. The volume of the metered blood is the volume of the sample storage well 41b and the volume of the sample storage conduit 83b. When the cap 50b is fully inserted into cap latch recess 73b, the cartridge in the sealed configuration. A person of ordinary skill will appreciate that an overflow well like 47b is useful for keeping all the blood in a contained system to avoid blood contamination of the analyzer, but it is not essential for the function of the cartridge or the metering system described herein.

In another step, the cartridge in the sealed configuration is inserted in the slot or receptor of the analyzer (not shown). The steps following cartridge insertion are automatically performed by the analyzer, and comprise depression of the flexible member 345b. The flexible member 345b can also be repeatedly depressed and released causing the blood to move forward and backward, in order to dissolve the dry one or more reagent in the blood sample. Depression or (repeated depression followed by release) of the flexible member 345b may be performed by a small stepper motor mounted on the receptor of the analyzer, but other means may be used that is known by a person skilled in the art. In the case of cartridge 10b, having an optional mixing chamber 89, the turbulence created as the blood sample flows into the mixing chamber 89 is sufficient to dissolve the one or more reagent, depending on the nature of the one or more reagent. It is known that some lyophilized reagents in relatively small quantities will dissolve almost immediately after the blood sample makes contact with the lyophilized substance, for example thromboplastin, used for measuring prothrombin time. It is also known that some reagents can be coated on the walls of a conduit, and more mixing is required to dissolve the reagents from the conduit walls.

In the case of cartridge 10, which has an optical detection chamber, another step is to apply a pre-developed calibration algorithm (see for example, U.S. Pat. No. 6,651,015 which is incorporated herein by reference) for hematocrit measurement to the optical measurement of the unclotted or clotted blood at one or more than one wavelength, and using the hematocrit measurement to correct the PT-INR for the patient's hematocrit.

Sample Measurement (Using Cartridges 10c and 10d as Non-Limiting Examples)

Disposable cartridges 10c and 10d for measuring a property of a sample, the cartridge having rapid sample metering systems, will now be described. The detection system is optical, but other embodiments of similar cartridges use different detection systems.

Shown in FIG. 9A is an exploded view of the disposable cartridge 10c for measuring a property of a sample, the cartridge having a rapid sample metering system, according to a third embodiment of the cartridge. This embodiment is similar to cartridge 10b and the major differences are as follows: a) The detection system is optical instead of electrochemical; b) The latch 70c is a pivotal latch having a pivot 62c, instead of a stationary latch 70b illustrated collectively in FIGS. 7A-7D; c) The sample storage conduit 83c is disposed at the bottom of the second housing member 30c, defined by a groove 85c (see FIG. 9H) and a bottom cover 351c; and d) The cap 50c is designed differently and discussed in greater details later. Other differences will become apparent as the other drawings are described and viewed in conjunction with description of structural features provided in Table 1.

Shown in FIG. 9B is a bottom view of the first housing member 20c of the cartridge shown in FIG. 9A. Shown in FIG. 9C is the bottom view of the first housing member 20c shown in FIG. 9B, overlaid by and in alignment with the gasket 100c shown in FIG. 9A. Shown in FIG. 9D is a top view of the second housing member 30c of the cartridge shown in FIG. 9A. Shown in FIG. 9E is the top view of the second housing member 30c shown in FIG. 9D, overlaid by and in alignment with the gasket 100c shown in FIG. 9A.

Figure 9F:
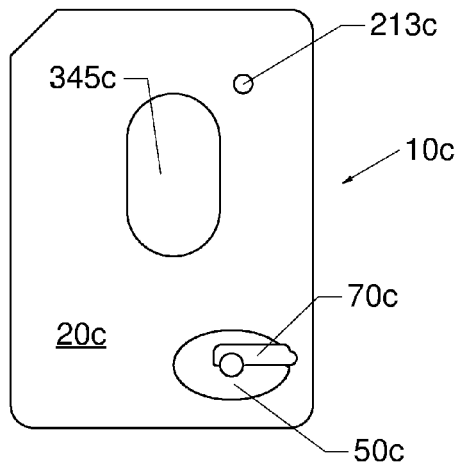
FIG. 9F is a top view of the cartridge 10c shown in FIG. 9A, with the cap 50c in a fully closed and latched position.
Figure 9J:
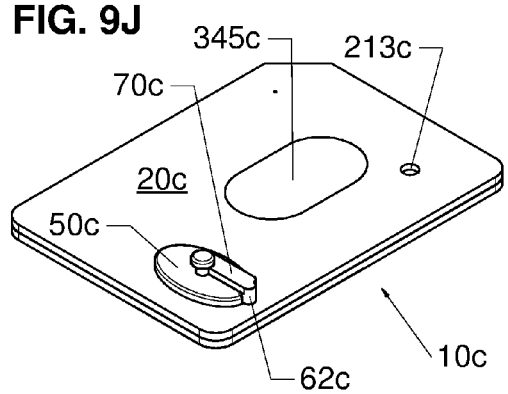
FIG. 9J is a perspective top view of the cartridge 10c shown in FIG. 9F.
Figure 9G:
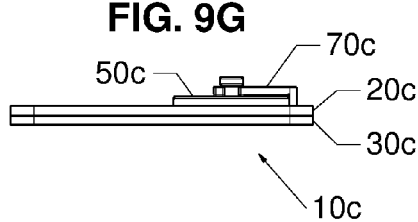
FIG. 9G is a front view of the cartridge 10c shown in FIG. 9F.
Figure 9K:
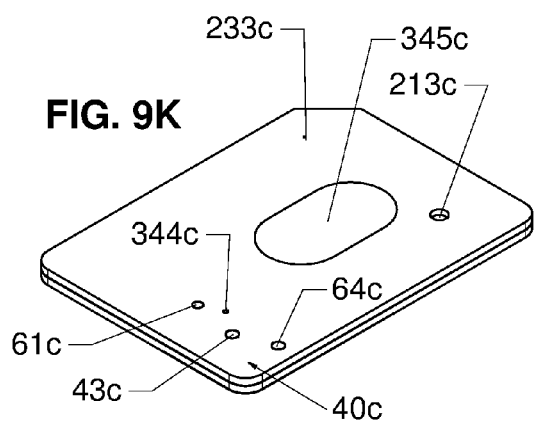
FIG. 9K is the perspective top view of the cartridge 10c shown in FIG. 9J. with the cap 50c and latch 70c removed.
Figure 9H:
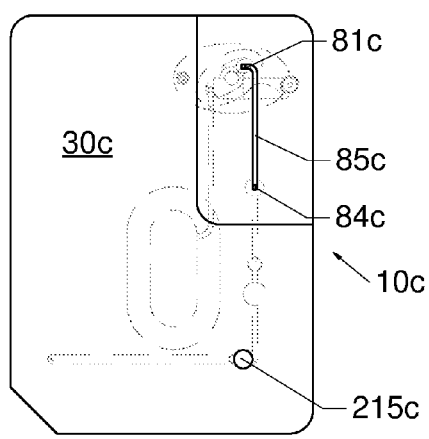
FIG. 9H is a bottom view of the cartridge 10c shown in FIG. 9F, with bottom cover 351c removed to expose the sample storage conduit groove 85c.

Shown in FIG. 9F is a top view of the cartridge 10c shown in FIG. 9A, with the cartridge 10c in a sealed configuration and latch 70c engaged with the cap 50c. Shown in FIG. 9G is a front view of the cartridge 10c shown in FIG. 9F. Shown in FIG. 9H is a bottom view of the cartridge 10c shown in FIG. 9F, with bottom cover 351c removed to expose sample storage conduit entrance 81c, the sample storage conduit groove 85c, and the junction of sample storage conduit 83c and capillary break 87c (see FIG. 11B). Shown in FIG. 9J is a perspective view of the cartridge 10c shown in FIG. 9F. Shown in FIG. 9K is the perspective view of the cartridge 10c shown in FIG. 9J. with the cap 50c and latch 70c hidden.

Figure 9L:
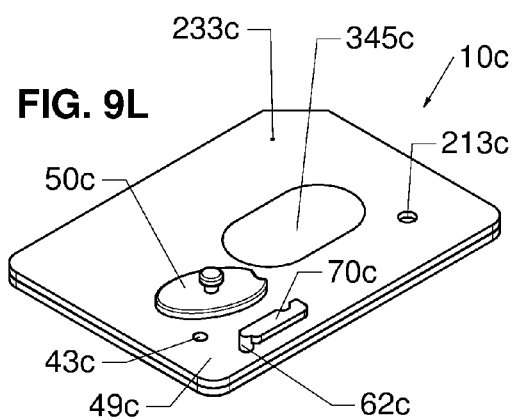
FIG. 9L is a top view of the cartridge 10c shown in FIG. 9A, with the cap 50c in a fully open position.

Shown in FIG. 9L is a top view of the cartridge 10c shown in FIG. 9A, with the cartridge in an unsealed configuration. Latch 70c is shown swiveled clockwise about 90 degrees from its position shown in FIG. 9F, where the cartridge is shown in a sealed configuration.

Figure 10A:
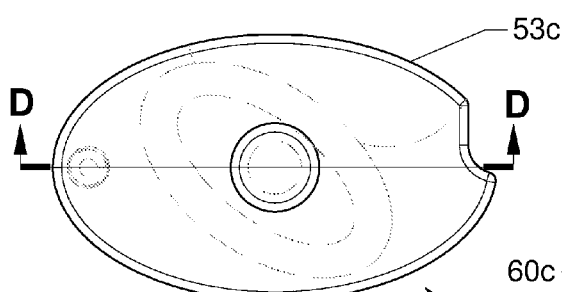
FIG. 10A is a top view of the cap 50c shown in FIGS. 9A, 9F, 9J and 9L.
Figure 10E:
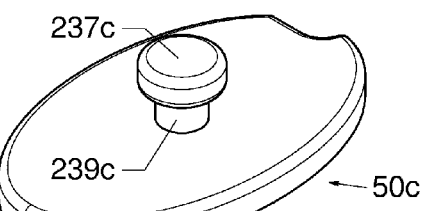
FIG. 10E is a perspective top view of the cap 50c shown in FIG. 10A.
Figure 10B:
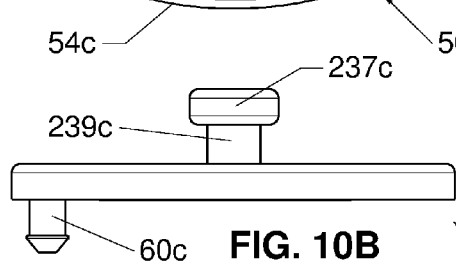
FIG. 10B is a front view of the cap 50c shown in FIG. 10A.

Illustrated collectively in FIGS. 10A-10H are details of the cap 50c. Shown in FIG. 10A is a top view of the cap 50c shown in FIGS. 9A, 9F, 9J and 9L, showing a sweeping portion 53c and a trailing portion 54c of cap 50c. Shown in FIG. 10B is a front view of the cap 50c shown in FIG. 10A, showing a pin 60c for hingedly attaching the cap to the sample inlet portion 40c and allowing the cap to swing with the gasket 57c frictionally engaged with the surface 49c of inlet portion 40c. Also shown is a crown 237c and a neck 239c of a cap knob of cap 50c, the neck 239c used for engaging the latch 70c and the crown 237c used for handling the cap 50c.

Figure 10F:
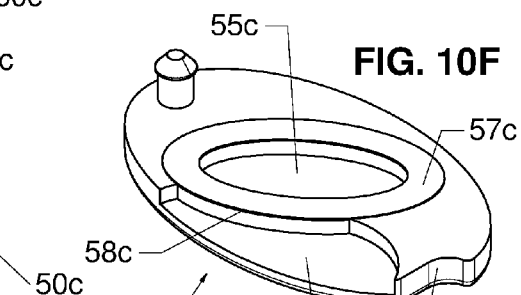
FIG. 10F is a perspective bottom view of the cap 50c shown in FIG. 10C.
Figure 10C:
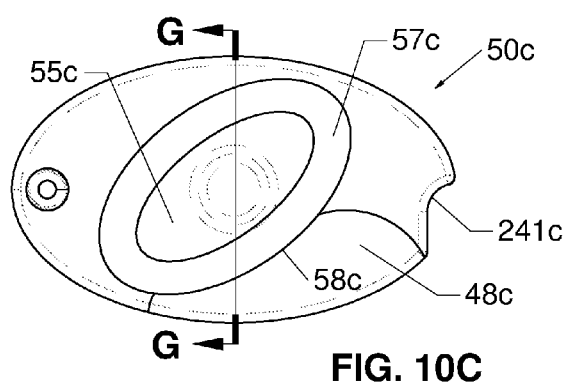
FIG. 10C is a bottom view of the cap 50c shown in FIG. 10A.
Figure 10G:
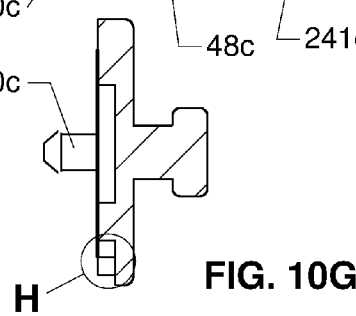
FIG. 10G is a cross-sectional view through the cap 50c shown in FIG. 10C along line G-G.
Figure 10D:
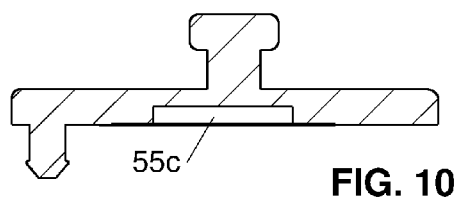
FIG. 10D is a cross-sectional view through the cap 50c shown in FIG. 10A along line D-D.
Figure 10H:
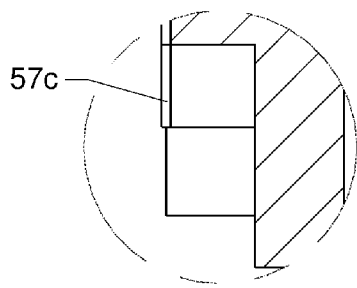
FIG. 10H is a detailed view of detail H of the cap 50c shown in FIG. 10G.

Shown in FIG. 10C is a bottom view of the cap 50c shown in FIG. 10A, showing a cap recess 55c, the gasket 57c, a groove 48c disposed at the underside and at the sweeping portion 53c of the cap 50c, for storing excess sample. Also shown is a sweeping cap edge 58c disposed at the sweeping portion 53c of cap 50c for skimming off excess sample, and a notch 241c in cap 50c for mating with pivot 62c of latch 70c, when cartridge 10c is in a sealed configuration. Shown in FIG. 10D is a cross-sectional view through the cap 50c shown in FIG. 10A along line D-D. Shown in FIG. 10E is a perspective view of the cap 50c shown in FIG. 10A. Shown in FIG. 10F is a perspective view of the cap 50c shown in FIG. 10C. Shown in FIG. 10G is a cross-sectional view through the cap 50c shown in FIG. 10C along line G-G. Shown in FIG. 10H is a detailed view of detail H of the cap 50c shown in FIG. 10G, showing the gasket 57c slighted elevated above the rest of the underside of the cap for creating the sweeping cap edge 58c.

Shown in FIG. 11A is a top view of the cartridge 10c (similar to the view shown in FIG. 9F) with the cartridge in a sealed configuration, for illustrating the internal structure. Shown in FIG. 11B is a first enlarged cross-sectional view through the cartridge 10c shown in FIG. 11A along line B-B. It should be noted that sufficient clearance between the crown 237c of the cap knob and the latch 70c is provided, and latch 70c is in contact with the cap 50c, for the latch 70c to apply force on the cap 50c when the cartridge in a sealed configuration. Also shown in FIG. 11B is the separate reagent chamber 209c and mixing chamber 89c. The perspective and top view of the reagent chamber 209c and the portion 89c" of mixing chamber 89c in a second housing member 30c, are shown in FIG. 9A and FIG. 9D respectively. The volume of the mixing chamber is substantially larger than the volume of the reagent chamber, and the two chambers are fluidly connected by a narrow conduit 210c. After the sample fills the reagent chamber 209c containing the dry reagent, the reagent and sample are mixed more thoroughly after the partially mixed sample and reagent are ejected into the larger mixing chamber 89c, by turbulence. Shown in FIG. 11C is a second enlarged cross-sectional view through the cartridge 10c shown in FIG. 11A along line C-C, showing the optical chamber 211c and having an overflow conduit 227c and a vent 233c for relieving pressure and therefore allowing flow. Shown in FIG. 11D is a third enlarged cross-sectional view through the cartridge 10c shown in FIG. 11A along line D-D. Shown in FIG. 11E is a fourth enlarged cross-sectional view through the cartridge 10c shown in FIG. 11A along line E-E. By way of example, latch 70c is engaged with cap 50c in a similar manner as illustrated in FIG. 6F, for the engagement of cap 50b in cartridge 10b.

Figure 12A:
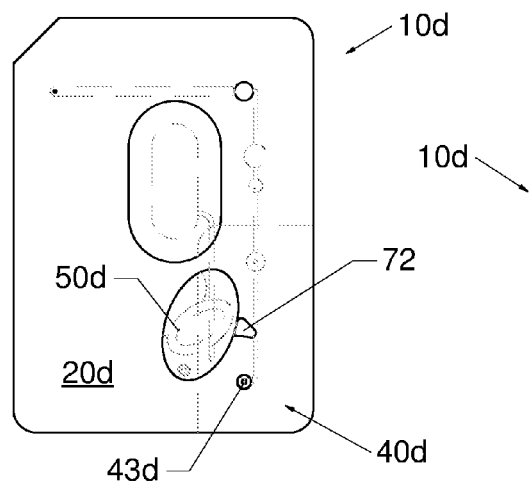
FIG. 12A is top view of the disposable cartridge 10d for measuring a property of a sample, the cartridge having a rapid sample metering system, according to a fourth embodiment of the cartridge, in a fully open position.

Shown in FIG. 12A is top view of the disposable cartridge 10d for measuring a property of a sample, the cartridge having a rapid sample metering system, according to a fourth embodiment of the cartridge, in an unsealed configuration. Cartridge 10d is like cartridge 10c illustrated collectively in FIGS. 9A-9L. The major differences are: a) The cap 50d does not have a knob (239c & 237C) or a notch 241c; b) The cartridge 10c does not have a latch 70c; and c) The cartridge 10d comprises a cap stop for keeping cartridge 10d in either an unsealed configuration or a sealed configuration.

Figure 12B:
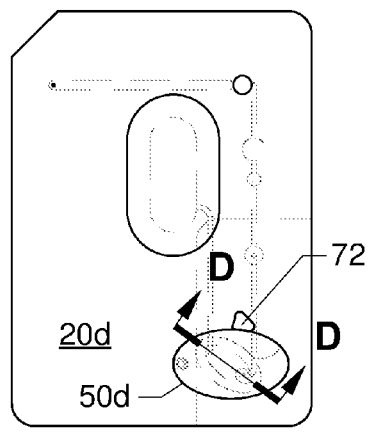
FIG. 12B is top view of the disposable cartridge 10d shown in FIG. 12A, but in a fully closed position.
Figure 12C:
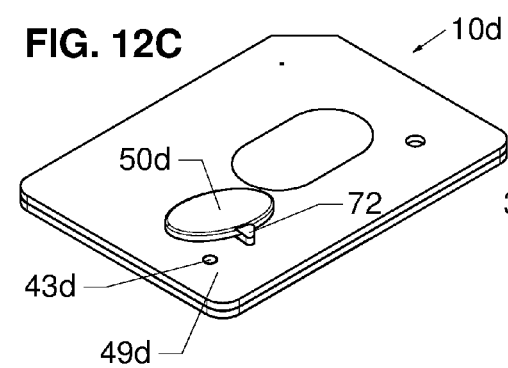
FIG. 12C is perspective top view of the disposable cartridge 10d shown in FIG. 12A (in a fully open position)

Shown in FIG. 12B is top view of the disposable cartridge 10d shown in FIG. 12A, but in a sealed configuration. Shown in FIG. 12C is perspective view of the disposable cartridge 10d shown in FIG. 12A (in an unsealed configuration).

Figure 12D:
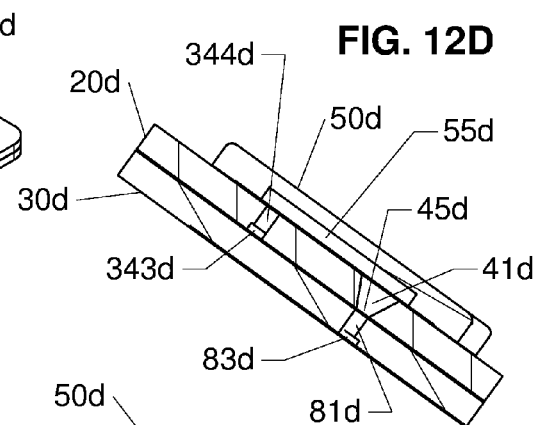
FIG. 12D is an enlarged cross-sectional view through the cartridge 10d shown in FIG. 12B along line D-D.

Shown in FIG. 12D is an enlarged cross-sectional view through the cartridge 10d shown in FIG. 12B along line D-D, showing the cap recess 55d providing a closed air passage connecting the air bladder exit port 344d and the sample storage well 41d for communicating the pressurized air from the air bladder exit port to the sample storage well for urging the sample into the reagent chamber (See 209c in FIG. 11B for cartridge 10c), the mixing chamber (See 89c in FIG. 11B for cartridge 10c), and the optical chamber (See 211c in FIG. 11C for cartridge 10c), in that order.

Figure 13A:
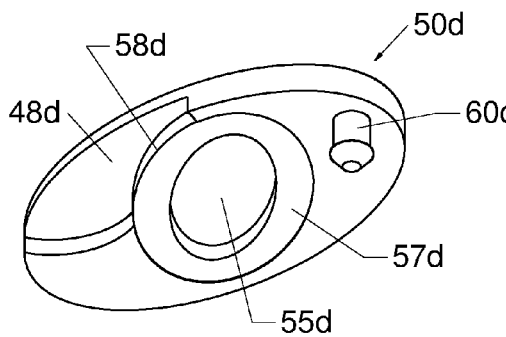
FIG. 13A is a first perspective bottom view of the cap 50d shown in FIG. 12A, showing the underside.
Figure 13B:
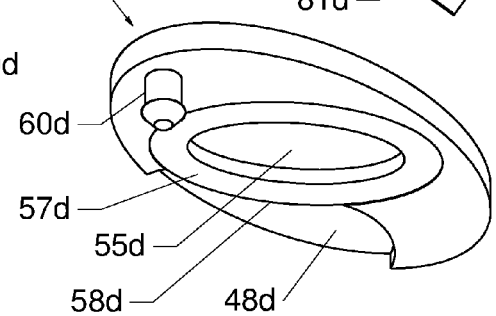
FIG. 13B, is a second perspective bottom view of the cap 50d shown in FIG. 12A, showing the underside.

Shown in FIG. 13A is a first perspective view of the cap 50d shown in FIG. 12A, showing the underside, and shown in FIG. 13B is a second perspective view of the cap 50d shown in FIG. 12A, showing the underside.

Sample Measurement

The following is a brief description of a system for metering a sample and measuring a property of the sample, using one of the cartridges previously described explicitly or implicitly. The system comprising further comprises an analyzer. The analyzer comprises: a) a receptor for receiving the cartridge; b) one or more than one processor for controlling the analyzer; and c) means for activating the air bladder; and a detector for receiving the signal from the detection chamber and sending the signal to the one or more than one processor for transforming the signal into the property of the sample.

The following is a description of a method for measuring a property of a blood sample, using one of the cartridges previously described explicitly or implicitly. The method comprises: a) providing the cartridge; b) providing an analyzer comprising: 1) a receptor for receiving the cartridge; 2) one or more than one processor for controlling the analyzer; 3) means for activating the air bladder; and 4) a detector for receiving the signal from the detection chamber and sending the signal to the one or more than one processor for transforming the signal into the property of the sample; c) obtaining a blood sample by pricking a body part; depositing the blood sample into the sample storage well; d) rotating the cartridge cap about the pin and skimming off excess blood; e) arranging the cartridge in a sealed configuration, wherein the cap recess facilitates provision of a closed air passage connecting the air bladder exit port and the sample storage well for communicating pressurized air from the air bladder exit port to the sample storage well for urging the blood towards the detection chamber; f) inserting the sealed cartridge into the analyzer receptor; g) activating the air bladder for providing the pressurized air; h) dissolving the one or more than one reagent into the blood; i) urging the mixture of blood and the one or more than one reagent into the detection chamber; and j) measuring the property of the blood sample.

Some methods for measuring a property of a blood sample, for example prothrombin time (or activated clotting time), further comprise: a) providing a cartridge further comprising an optical chamber; b) providing an analyzer further comprising a source of electromagnetic radiation and a detector for collecting electromagnetic radiation transmitted through the optical chamber or reflected from the optical chamber; c) applying a pre-determined calibration algorithm to the collected electromagnetic radiation to measure hematocrit of the blood sample to produce a hematocrit measurement; and d) using the hematocrit measurement to correct the property of the blood sample, for example prothrombin time (or activated clotting time), for the actual plasma volume in the blood sample.

While the above description provides example embodiments, it will be appreciated that the present invention is susceptible to modification and change without departing from the fair meaning and scope of the accompanying claims. Accordingly, what has been described is merely illustrative of the application of aspects of embodiments of the invention. Numerous modifications and variations of the present invention are possible in light of the above teachings. It is therefore to be understood that within the scope of the appended claims, the invention may be practiced otherwise than as specifically described herein. Furthermore, the discussed combination of features might not be absolutely necessary for the inventive solution.

I claim:

1. A disposable cartridge comprising,
   a cartridge body comprising an upper surface and a lower surface;
   a cap pivotally connected to the cartridge body by a pin, the cap positioned on the upper surface of the cartridge body, the cap comprising a top side and an underside, the underside comprising a cap recess surrounded by a flat surface;
   a sample inlet portion located on the upper surface, the sample inlet portion comprising:
      a sample storage well for storing a first portion of a sample, the sample storage well comprising a top portion for receiving the sample and a bottom portion for releasing a second portion of the sample to a sample storage conduit;
      an air bladder exit port;
      a pin hole for receiving the pin, and
      a sliding surface surrounding the sample storage well and the air bladder exit port, the sliding surface for frictionally engaging the flat surface of the underside of the cap;
   the cap comprising a sweeping edge for skimming off any excess of the sample from the sample storage well or sample inlet portion when the cap is pivotally rotated from an open position where the cartridge is in an unsealed configuration, to a closed positioned where the cartridge is in a sealed configuration;
   an air bladder fluidly connected with the air bladder exit port;
   the sample storage conduit in fluid communication between the bottom portion of the sample well and a capillary break, the sample storage conduit for receiving the second portion of the sample, the total volume of the sample in the cartridge in the sealed configuration is equivalent to the volume measured from the top portion of the sample storage well to the capillary break;
   a detection chamber in fluid communication with the capillary break and the sample storage conduit via a detection chamber inlet conduit, the detection chamber for receiving a portion of the total volume of the sample from the sample storage conduit and for generating a signal during sample interrogation, the signal used to calculate a property of the sample; and
   a vent in fluid communication with the detection chamber, the vent for relieving pressure in the detection chamber;
   wherein, in the unsealed configuration the sample storage well is open and available to receive the sample, and in the sealed configuration the cap recess facilitates provision of a closed air passage connecting the air bladder exit port and the sample storage well for communicating pressurized air from the air bladder to the sample storage well via the air bladder exit port, so that when the air bladder is pressed, the volume of the sample, or a portion thereof, is urged from the sample storage conduit into the detection chamber.

2. The disposable cartridge according to claim 1, wherein the sample inlet portion further comprises at least one cap stop, for defining the unsealed configuration and the sealed configuration.

3. The disposable cartridge according to claim 1, wherein the top portion of the sample storage well is substantially larger than the bottom portion of the sample storage well.

4. The disposable cartridge according to claim 1, further comprising at least one reagent in the detection chamber inlet conduit disposed between the sample storage conduit and the detection chamber.

5. The disposable cartridge according to claim 1, further comprising a mixing chamber disposed between an end of the sample storage conduit adjacent to the capillary break and the detection chamber.

6. The disposable cartridge according to claim 5, further comprising a reagent chamber containing at least one reagent, the reagent chamber disposed adjacent to the mixing chamber, whereby passage of the total volume of the sample through the reagent chamber produces a partially mixed sample comprising the at least one reagent, and passage of the partially mixed sample into the mixing chamber results in a more efficient mixing of the sample.

7. The disposable cartridge according to claim 6, wherein the mixing chamber is substantially larger than the reagent chamber.

8. The disposable cartridge according to claim 1, wherein the sample inlet portion further comprises a sample overflow well for receiving excess sample.

9. The disposable cartridge according to claim 1, further comprising a groove disposed at the underside of the cap in front of the sweeping edge of the cap, for holding excess sample.

10. The disposable cartridge according to claim 1, further comprising a gasket positioned on the flat surface.

11. The disposable cartridge according to claim 10, wherein the sweeping edge is an outer edge of the gasket.

12. The disposable cartridge according to claim 1, further comprising a latch for securing the cap when the cartridge is in the sealed configuration.

13. The disposable cartridge according to claim 12, wherein the latch is a stationary structure anchored in the sample inlet portion.

14. The disposable cartridge according to claim 12, wherein the latch is pivotally attached to the sample inlet portion.

15. The disposable cartridge according to claim 4, wherein the at least one reagent is selected from dry thromboplastin, celite, and kaolin.

16. A system for metering a sample and measuring a property of the sample, the system comprising the disposable cartridge according to claim 1, and an analyzer, the analyzer comprising:
   a receptor for receiving the disposable cartridge;
   one or more than one processor for controlling the analyzer;
   means for activating the air bladder; and
   a detector for receiving the signal from the detection chamber and sending the signal to the one or more than one processor for transforming the signal into the property of the sample.

17. A method for measuring a property of a blood sample comprising:
   depositing a blood sample into the sample storage well of the disposable cartridge as defined in claim 4, the disposable cartridge in the unsealed configuration;
   rotating the cartridge cap about the pin and skimming off excess blood and arranging the disposable cartridge in the sealed configuration to produce a sealed cartridge comprising the total volume of the sample;
   inserting the sealed cartridge into a receptor of an analyzer, the analyzer comprising:
   the receptor for receiving the disposable cartridge;
   one or more than one processor for controlling the analyzer;
   means for activating the air bladder; and
   a detector for receiving the signal from the detection chamber and sending the signal to the one or more than one processor for transforming the signal into the property of the sample;
   activating the air bladder to provide the pressurized air and move the total volume of the sample through one of the detection chamber inlet conduit and a reagent chamber disposed between an end of the sample storage conduit adjacent to the capillary break and the detection chamber, containing the at least one reagent, thereby dissolving the at least one reagent into the blood to produce a mixture of the blood and the at least one reagent;
   urging a portion of the mixture of blood and the at least one reagent into the detection chamber; and
   measuring the property of the blood sample in the detection chamber using the analyzer.

18. The method as defied in claim 17 wherein, the property of the blood sample being measured is prothrombin time, or activated clotting time;
   the detection chamber of the disposable cartridge comprises an optical chamber, and the analyzer comprises a source of electromagnetic radiation that is directed to the optical chamber; the detector is configured to collect electromagnetic radiation that is transmitted through the optical chamber, or reflected from the optical chamber;
   in the step of measuring, a pre-determined calibration algorithm is applied to the collected electromagnetic radiation to measure hematocrit of the blood sample to produce a hematocrit measurement; and using the hematocrit measurement to correct the prothrombin time for an actual plasma volume in the blood sample.

19. A method according to claim 17, wherein the at least one reagent is dry thromboplastin, and the property of the blood is prothrombin time.

20. A method according to claim 17, wherein the at least one reagent is one of celite and kaolin, and the property of the blood is activated clotting time.

* * * * *